United States Patent
Kim et al.

(10) Patent No.: US 9,520,566 B2
(45) Date of Patent: Dec. 13, 2016

(54) CONDENSED CYCLIC COMPOUND AND ORGANIC LIGHT-EMITTING DIODE COMPRISING THE SAME

(71) Applicants: Samsung Display Co., Ltd., Yongin, Gyeonggi-Do (KR); Duksan High Metal Co., Ltd., Ulsan (KR)

(72) Inventors: Seul-Ong Kim, Yongin (KR); O-Hyun Kwon, Yongin (KR); Dong-Woo Shin, Yongin (KR); Mie-Hwa Park, Yongin (KR); Bum-Sung Lee, Ulsan (KR)

(73) Assignees: Samsung Display Co., Ltd., Samsung-ro, Giheung-Gu, Yongin-si, Gyeonggi-Do (KR); DUK SAN NEOLUX CO., LTD., Ssukgol-Gil, Ipjang-Myeon, Seobuk-Gu, Cheonan-Si, Chungcheongnam-Do (KR)

( * ) Notice: Subject to any disclaimer, the term of this patent is extended or adjusted under 35 U.S.C. 154(b) by 669 days.

(21) Appl. No.: 14/012,073

(22) Filed: Aug. 28, 2013

(65) Prior Publication Data

US 2014/0197384 A1    Jul. 17, 2014

(30) Foreign Application Priority Data

Jan. 16, 2013    (KR) .................... 10-2013-0005112

(51) Int. Cl.
  *H01L 51/00*    (2006.01)
  *C09K 11/06*    (2006.01)
  (Continued)

(52) U.S. Cl.
  CPC ......... *H01L 51/0054* (2013.01); *C07D 249/08* (2013.01); *C09K 11/06* (2013.01);
  (Continued)

(58) Field of Classification Search
  CPC .................................................. H01L 51/0054
  See application file for complete search history.

(56) References Cited

U.S. PATENT DOCUMENTS 7,405,326 B2    7/2008 Kawamura et al.
2007/0212568 A1    9/2007 Wang
(Continued)

FOREIGN PATENT DOCUMENTS

KR    10-2006-0134979 A    12/2006
KR    10-2008-0034137 A    4/2008
KR    10-2011-0064222 A    6/2011

*Primary Examiner* — Robert Vetere
(74) *Attorney, Agent, or Firm* — Robert E. Bushnell, Esq.

(57) ABSTRACT

A condensed cyclic compound represented by Formula 1 below and an organic light-emitting device (OLED) including the condensed cyclic compound are presented.

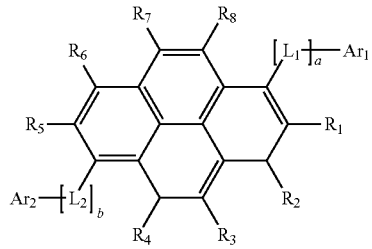

$Ar_1$ and $Ar_2$ in Formula 1 are each independently one of a hydrogen atom, an aryl or heteroaryl group and an arylamino group, at least one of $Ar_1$ and $Ar_2$ being a substituted or unsubstituted 1,2,4-triazol-4-yl group; $L_1$ and $L_2$ in Formula 1 are linking groups, each independently one of a cyclic or noncyclic, saturated or unsaturated hydrocarbon group and a heteroarylene group; a and b in Formula 1 are each
(Continued)

independently one of 0 or 1; and $R_1$ to $R_8$ in Formula 1 being each independently one of a variety of inorganic and organic substituents including cyclic or noncyclic, saturated or unsaturated and aromatic, nonaromatic or heteroaromatic groups. The OLED may have a low driving voltage, a high emission efficiency and long lifespan characteristics.

18 Claims, 1 Drawing Sheet

(51) Int. Cl.
*C07D 249/08* (2006.01)
*H01L 51/50* (2006.01)

(52) U.S. Cl.
CPC .. *H01L 51/0067* (2013.01); *C09K 2211/1416* (2013.01); *H01L 51/0058* (2013.01); *H01L 51/5012* (2013.01); *H01L 2251/308* (2013.01)

(56) References Cited

U.S. PATENT DOCUMENTS

| | | | | |
|---|---|---|---|---|
| 2008/0049413 A1* | 2/2008 | Jinde | ............... | C09K 11/06 362/84 |
| 2008/0166593 A1* | 7/2008 | Stoessel | ............... | C09K 11/06 428/704 |

\* cited by examiner

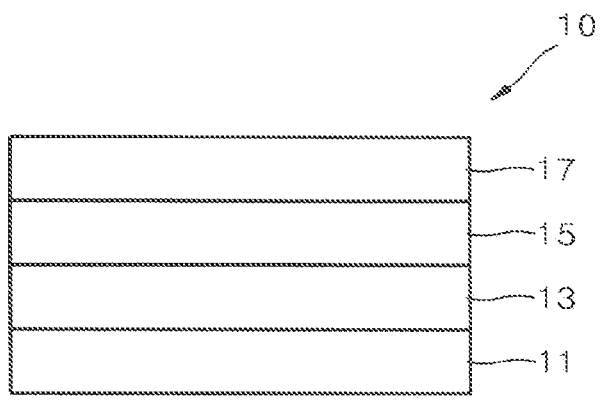

CONDENSED CYCLIC COMPOUND AND ORGANIC LIGHT-EMITTING DIODE COMPRISING THE SAME

CLAIM OF PRIORITY

This application makes reference to, incorporates the same herein, and claims all benefits accruing under 35 U.S.C. §119 from an application for CONDENSED CYCLIC COMPOUND AND ORGANIC LIGHT-EMITTING DIODE COMPRISING THE SAME, earlier filed in the Korean Intellectual Property Office on 16 Jan. 2013 and there duly assigned Serial No. 10-2013-0005112.

BACKGROUND OF THE INVENTION

1. Field of the Invention

One or more embodiments of the present invention relate to a condensed cyclic compound and an organic light-emitting device including the condensed cyclic compound.

2. Description of the Related Art

Organic light-emitting devices (OLEDs), which are self-emitting devices, have advantages such as wide viewing angles, excellent contrast, quick response, high brightness and excellent driving voltage characteristics, and they can provide multicolored images.

A typical OLED has a structure including a substrate and an anode, a hole transport layer (HTL), an emission layer (EML), an electron transport layer (ETL), and a cathode, which are sequentially stacked on the substrate. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

In view of the advantages of these OLEDs, there has been a demand for the development of novel materials for organic light-emitting devices that can provide the devices with characteristics of high luminance, high efficiency, and long lifetime.

SUMMARY OF THE INVENTION

One or more embodiments of the present invention include a novel condensed cyclic compound for organic light-emitting devices having low voltage, high luminance, high efficiency, high color purity, and long lifetime, and an organic light-emitting device having an organic layer containing the condensed cyclic compound.

Additional aspects of the present invention will be set forth in part in the description which follows and, in part, will be apparent from the description, or may be learned by practice of the presented embodiments.

According to one or more embodiments of the present invention, provided is a condensed cyclic compound of Formula 1 below:

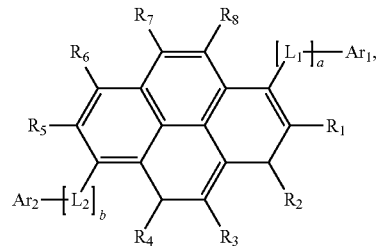

Formula 1

$Ar_1$ and $Ar_2$ in Formula 1 being each independently one of a hydrogen atom, a substituted or unsubstituted $C_6$-$C_{60}$ aryl group, a substituted or unsubstituted $C_2$-$C_{60}$ heteroaryl group and a substituted or unsubstituted $C_1$-$C_{60}$ arylamino group, at least one of $Ar_1$ and $Ar_2$ being a substituent represented by Formula 2F below:

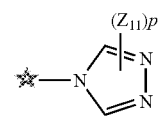

Formula 2F $Z_{11}$ being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other;

p being an integer selected from 1 to 4;

★ indicating a binding site; $L_1$ and $L_2$ in Formula 1 being each independently one of a substituted or unsubstituted $C_1$-$C_{60}$ alkylene group, a substituted or unsubstituted $C_3$-$C_{60}$ cycloalkylene group, a substituted or unsubstituted $C_2$-$C_{60}$ alkenylene group, a substituted or unsubstituted $C_5$-$C_{60}$ cycloalkenylene group, a substituted or unsubstituted $C_2$-$C_{60}$ alkynylene group, a substituted or unsubstituted $C_5$-$C_{60}$ cycloalkynylene group, a substituted or unsubstituted $C_6$-$C_{60}$ arylene group and a substituted or unsubstituted $C_5$-$C_{60}$ heteroarylene group;

a and b in Formula 1 being each independently 0 or 1; and $R_1$ to $R_8$ in Formula 1 being each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, a substituted or unsubstituted $C_6$-$C_{60}$ arylthio group, —$N(Q_1)(Q_2)$ and —$Si(Q_3)(Q_4)(Q_5)$ (where $Q_1$ to $Q_5$ are each independently one of a $C_1$-$C_{60}$ alkyl group, a $C_1$-$C_{60}$ alkoxy group, a $C_6$-$C_{60}$ aryl group and a $C_2$-$C_{60}$ heteroaryl group).

According to one or more embodiments of the present invention, provided is an organic light-emitting device including: a first electrode; a second electrode disposed opposite to the first electrode; and an organic layer disposed between the first electrode and the second electrode, the organic layer comprising at least one of the condensed cyclic compounds of Formula 1 as described above.

BRIEF DESCRIPTION OF THE DRAWING

A more complete appreciation of the invention and many of the attendant advantages thereof will be readily apparent as the same becomes better understood by reference to the following detailed description when considered in conjunction with the accompanying drawings in which like reference symbols indicate the same or similar components, wherein:

FIG. 1 schematically illustrates the structure of an organic light-emitting device according to an embodiment of the present invention.

DETAILED DESCRIPTION OF THE INVENTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a condensed cyclic compound represented by Formula 1 below:

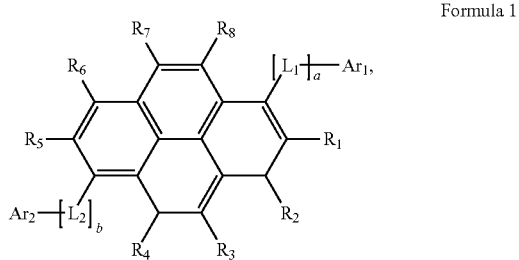

Formula 1

$Ar_1$ and $Ar_2$ in Formula 1 being each independently one of a hydrogen atom, a substituted or unsubstituted $C_6$-$C_{60}$ aryl group, a substituted or unsubstituted $C_2$-$C_{60}$ heteroaryl group and a substituted or unsubstituted $C_1$-$C_{60}$ arylamino group, at least one of $Ar_1$ and $Ar_2$ being a substituent represented by Formula 2F below:

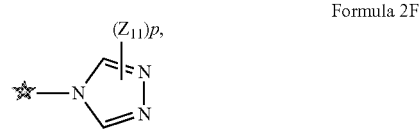

Formula 2F $Z_{11}$ in Formula 2F being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other;

p being an integer selected from 1 to 4;

★ indicating a binding site.

$L_1$ and $L_2$ in Formula 1 being each independently one of a substituted or unsubstituted $C_1$-$C_{60}$ alkylene group, a substituted or unsubstituted $C_3$-$C_{60}$ cycloalkylene group, a substituted or unsubstituted $C_2$-$C_{60}$ alkenylene group, a substituted or unsubstituted $C_5$-$C_{60}$ cycloalkenylene group, a substituted or unsubstituted $C_2$-$C_{60}$ alkynylene group, a substituted or unsubstituted $C_5$-$C_{60}$ cycloalkynylene group, a substituted or unsubstituted $C_6$-$C_{60}$ arylene group and a substituted or unsubstituted $C_5$-$C_{60}$ heteroarylene group;

a and b in Formula 1 being each independently 0 or 1; and $R_1$ to $R_8$ in Formula 1 being each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, a substituted or unsubstituted $C_6$-$C_{60}$ arylthio group, —$N(Q_1)(Q_2)$ and —$Si(Q_3)(Q_4)(Q_5)$ ($Q_1$ to $Q_5$ being each independently one of a $C_1$-$C_{60}$ alkyl group, a $C_1$-$C_{60}$ alkoxy group, a $C_6$-$C_{60}$ aryl group and a $C_2$-$C_{60}$ heteroaryl group).

In some embodiments, $Ar_1$ and $Ar_2$ in Formula 1 above may be each independently one of a hydrogen atom, a substituted or unsubstituted phenyl group, a substituted or unsubstituted biphenyl group, a substituted or unsubstituted terphenyl group, a substituted or unsubstituted pentaphenyl group, a substituted or unsubstituted a naphthyl group, a substituted or unsubstituted anthryl group, a substituted or unsubstituted pentalenyl group, a substituted or unsubstituted indenyl group, a substituted or unsubstituted azulenyl group, a substituted or unsubstituted indacenyl group, a substituted or unsubstituted acenaphthyl group, a substituted or unsubstituted heptalenyl group, a substituted or unsubstituted phenalenyl group, a substituted or unsubstituted a fluorenyl group, a substituted or unsubstituted phenanthrenyl group, a substituted or unsubstituted fluoranthenyl group, a substituted or unsubstituted pyrenyl group, a substituted or unsubstituted naphthacenyl group, a substituted or unsubstituted chrysenyl group, a substituted or unsubstituted triphenylenyl group, a substituted or unsubstituted perylenyl group, a substituted or unsubstituted picenyl group, a substituted or unsubstituted hexacenyl group, a substituted or unsubstituted spiro-fluorenyl group, a substituted or unsubstituted phenoxy group, a substituted or unsubstituted pyrrolyl group, a substituted or unsubstituted furyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted triazolyl group, a substituted or unsubstituted tetrazolyl group, a substituted or unsubstituted oxadiazolyl group, a substituted or unsubstituted a pyridyl group, a substituted or unsubstituted a pyrimidinyl group, a substituted or unsubstituted pyrazinyl group, a substituted or unsubstituted pyridazinyl group, a substituted or unsubstituted triazinyl group, a substituted or unsubstituted pyranyl group, a substituted or unsubstituted thiophenyl group, a substituted or unsubstituted thiazolyl group, a substituted or unsubstituted isothiazolyl group, a substituted or unsubstituted indolyl group, a substituted or unsubstituted isoindolyl group, a substituted or unsubstituted indolizinyl group, a substituted or unsubstituted benzofuryl group, a substituted or unsubstituted isobenzofuryl group, a substituted or unsubstituted indazolyl group, a substituted or unsubstituted benzimidazolyl group, a substituted or unsubstituted benzoxazolyl group, a substituted or unsubstituted benzisoxazolyl group, a substituted or unsubstituted imidazopyridyl group, a substituted or unsubstituted purinyl group, a substituted or unsubstituted quinolyl group, a substituted or unsubstituted isoquinolyl group, a substituted or unsubstituted phthalazinyl group, a substituted or unsubstituted quinazolinyl group, a substituted or unsubstituted quinoxalinyl group, a substituted or unsubstituted naphthyridinyl group, a substituted or unsubstituted cinnolinyl group, a substituted or unsubstituted benzothiophenyl group, a substituted or unsubstituted benzothiazolyl group, a substituted or unsubstituted carbazolyl group, a substituted or unsubstituted pyridoindolyl group, a substituted or unsubstituted dibenzofuryl group, a substituted or unsubstituted phenanthridinyl group, a substituted or unsubstituted benzoquinolyl group, a substituted or unsubstituted phenazinyl group, and a substituted or unsubstituted dibenzothiophenyl group, at least one of $Ar_1$ and $Ar_2$ being a substituted or unsubstituted 1,2,4-triazol-4-yl group as shown above.

For example, $Ar_1$ and $Ar_2$ may be each independently one of a hydrogen atom and a substituent represented by one of Formulae 2A to 2G below, at least one of $Ar_1$ and $Ar_2$ being represented by Formula 2F, but embodiments of the present invention are not limited thereto.

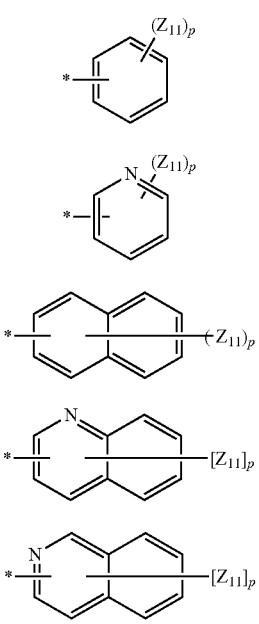

Formula 2A

Formula 2B

Formula 2C

Formula 2D

Formula 2E

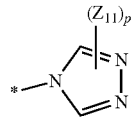

Formula 2F

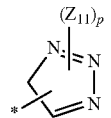

Formula 2G $Z_{11}$ may be one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other; p may be an integer from 1 to 7; and * indicates a binding site.

In some other embodiments, $Ar_1$ and $Ar_2$ may be each independently a group represented by one of Formulae 3A to 3J below, at least one of $Ar_1$ and $Ar_2$ being a group represented by Formula 3J below, but embodiments of the present invention are not limited thereto.

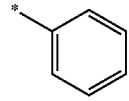

Formula 3A

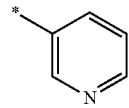

Formula 3B

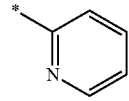

Formula 3C

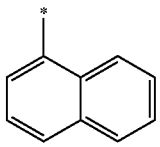

Formula 3E

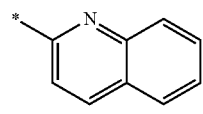

Formula 3F

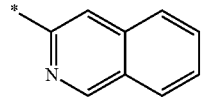

Formula 3G

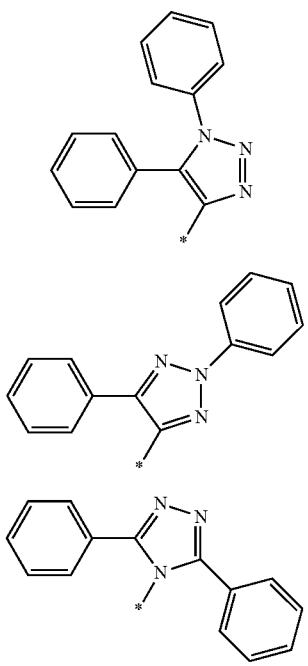

Formula 3H

Formula 3I

Formula 3J

In Formulae 3A to 3J, * indicates a binding site.

In Formula 1 above, $L_1$ and $L_2$ may be each independently one of a substituted or unsubstituted phenylene group, a substituted or unsubstituted naphthylene group, a substituted or unsubstituted phenanthrenylene group, a substituted or unsubstituted phenalenylene group, a substituted or unsubstituted pyrenylene group, a substituted or unsubstituted chrysenylene group, a substituted or unsubstituted anthrylene group, a substituted or unsubstituted pentalenylene group, a substituted or unsubstituted indenylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluoranthenylene group, a substituted or unsubstituted triphenylenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted fluorenylene group, a substituted or unsubstituted carbazolylene group, a substituted or unsubstituted dibenzopuranylene group, a substituted or unsubstituted dibenzothiophenylene group, a substituted or unsubstituted pyridylene group, a substituted or unsubstituted pyridazinylene group, a substituted or unsubstituted triazinylene group, a substituted or unsubstituted pyrrolylene group, a substituted or unsubstituted pyrazolylene group, a substituted or unsubstituted imidazolylene group, a substituted or unsubstituted imidazolinylene group, a substituted or unsubstituted triazolylene group, a substituted or unsubstituted tetrazolylene group, a substituted or unsubstituted imidazopyridinylene group, a substituted or unsubstituted imidazopyrimidinylene group, a substituted or unsubstituted pyrazinylene group, a substituted or unsubstituted pyrimidinylene group, a substituted or unsubstituted indolylene group, a substituted or unsubstituted purinylene group, a substituted or unsubstituted quinolinylene group, a substituted or unsubstituted phthalazinylene group, a substituted or unsubstituted indolizinylene group, a substituted or unsubstituted naphthyridinylene group, a substituted or unsubstituted quinazolinylene group, a substituted or unsubstituted cinnolinylene group, a substituted or unsubstituted indazolylene group, a substituted or unsubstituted phenazinylene group, a substituted or unsubstituted phenanthridinylene group, a substituted or unsubstituted pyranylene group, a substituted or unsubstituted chromenylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted isothiazolylene group, a substituted or unsubstituted benzoimidazolylene group, a substituted or unsubstituted isoxazolylene group and a substituted or unsubstituted oxadiazolylene group.

For example, $L_1$ and $L_2$ may be each independently one of a substituted or unsubstituted phenylene group, a substituted or unsubstituted a naphthyl group, a substituted or unsubstituted a pyridyl group, a substituted or unsubstituted pyrimidinylene group, a substituted or unsubstituted pyrazinylene group and a substituted or unsubstituted pyridazinylene group, but they are not limited thereto.

In Formula 1 above, $R_1$ to $R_8$ may be each independently one of a hydrogen atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a fluorenyl group, a dibenzofuranyl group, and a dibenzothiophenyl group; and one of a $C_1$-$C_{20}$ alkyl group, a $C_1$-$C_{20}$ alkoxy group, a phenyl group, a naphthyl group, an anthryl group, a fluorenyl group, a dibenzofuranyl group, and a dibenzothiophenyl group that are substituted with at least one of a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof.

For example, $R_1$ to $R_8$ may be each independently one of a hydrogen atom, a halogen atom, a methyl group, an ethyl group, a propyl group, a butyl group, a methoxy group, an ethoxy group, a propoxy group, a butoxy group, and a pentoxy group.

In some embodiments, in Formula 1 above of the condensed cyclic compound, $Ar_1$ and $Ar_2$ may be each independently one of a hydrogen atom and a substituent represented by one of Formulae 2A to 2F below, at least one of $Ar_1$ and $Ar_2$ being a substituent represented by Formula 2F:

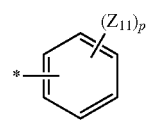

Formula 2A

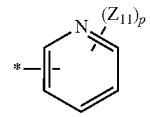

Formula 2B

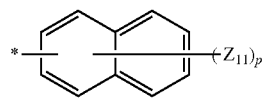

Formula 2C

-continued

Formula 2D

Formula 2E

Formula 2F

Formula 2G $Z_{11}$ may be one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other; p may be an integer from 1 to 7; and * indicates a binding site;

$L_1$ and $L_2$ may be each independently one of a phenylene group and a naphthyl group; L1 and L2 may be each independently one of a phenylene group and a naphthyl group that are substituted with one of a halogen atom, a hydroxy group, a cyano group, a methyl group, an ethyl group, a propyl group, a butyl group, a methoxy group and an ethoxy group;

$R_1$ to $R_8$ may be one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group.

In some other embodiments, in Formula 1 above of the condensed cyclic compound, $Ar_1$ and $Ar_2$ may be each independently a group represented by one of Formulae 3A to 3J, at least one of $Ar_1$ and $Ar_2$ being a group represented by Formula 3J:

Formula 3A

Formula 3B

Formula 3C

Formula 3D

Formula 3E

Formula 3F

Formula 3G

Formula 3H

Formula 3I

Formula 3J

When Ar1 and Ar2 in Formula 1 are each independently represented by Formulae 3A to 3J, $L_1$ and $L_2$ in Formula 1 may be each independently one of a phenylene group and a naphthylene group; and $R_1$ to $R_8$ in Formula 1 may be hydrogen atoms.

The condensed cyclic compound of Formula 1 may be one of Compounds 1 to 21 below, but is not limited thereto:

1

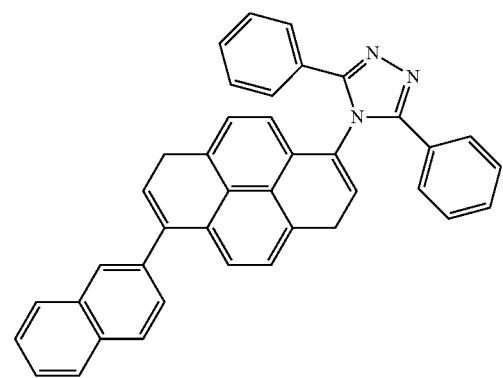
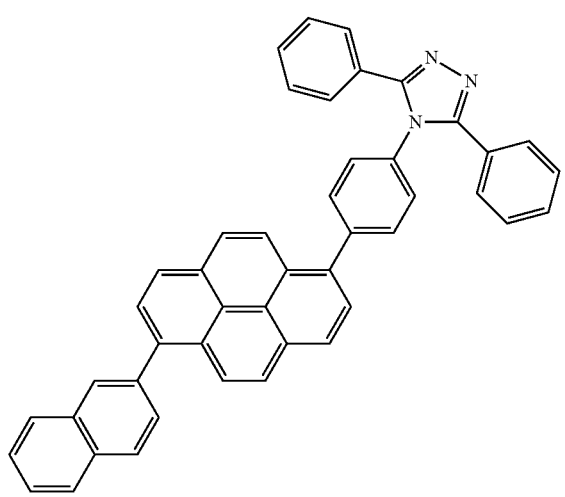
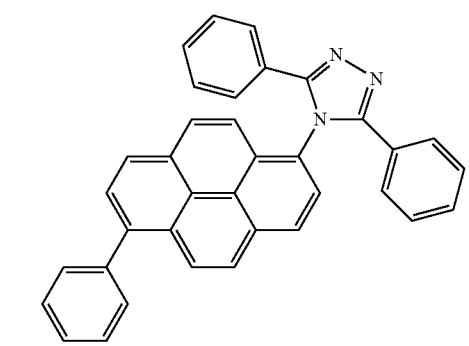
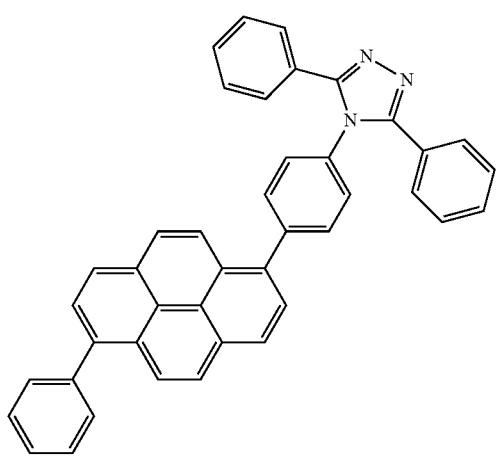
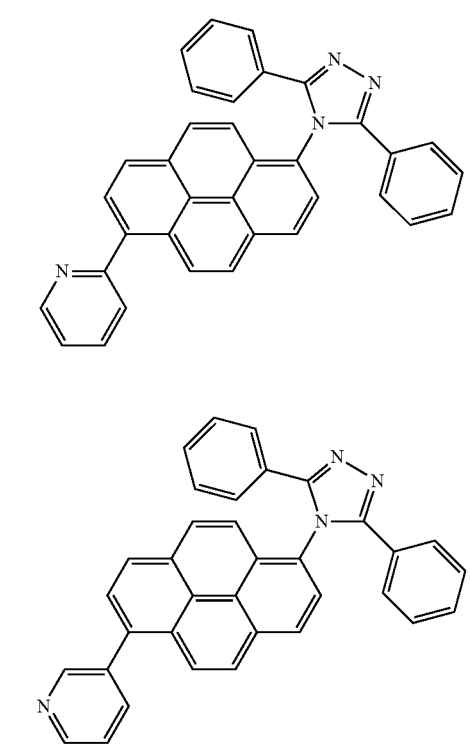
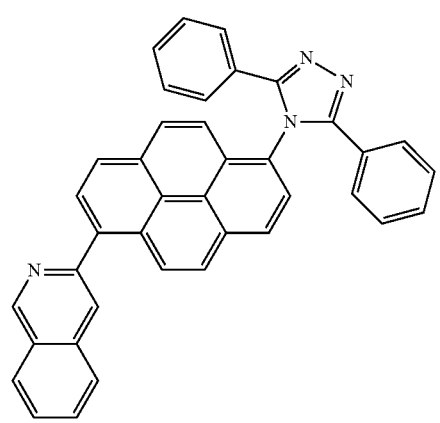

15
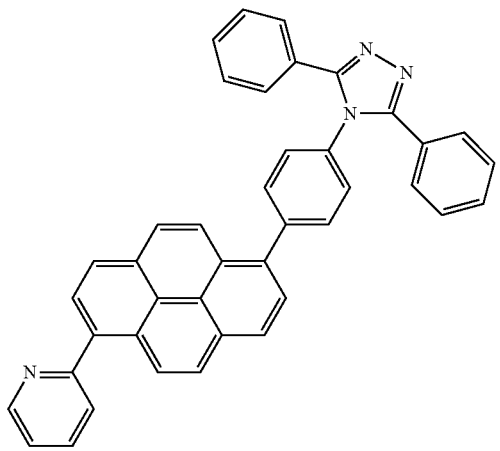
16
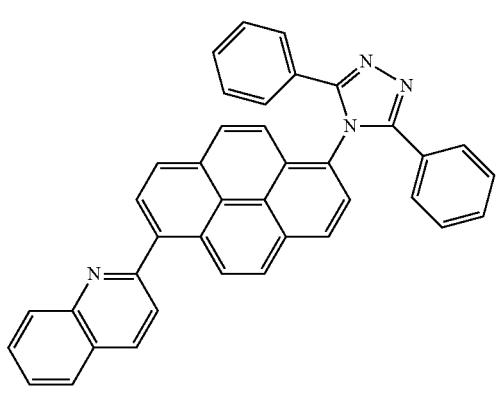
17
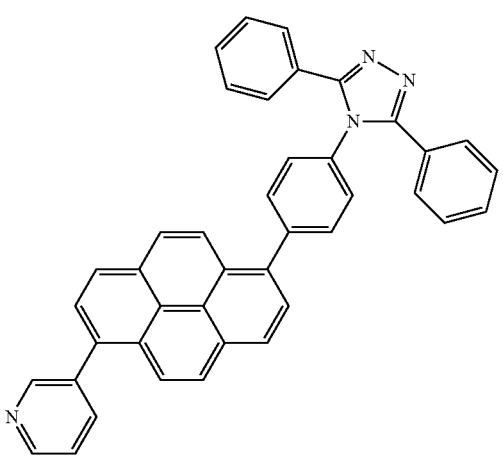
18
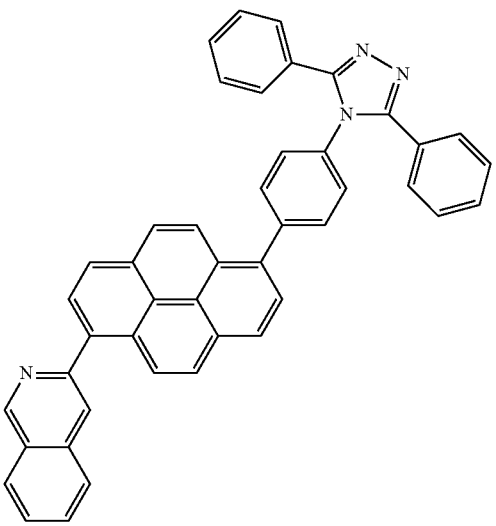
19
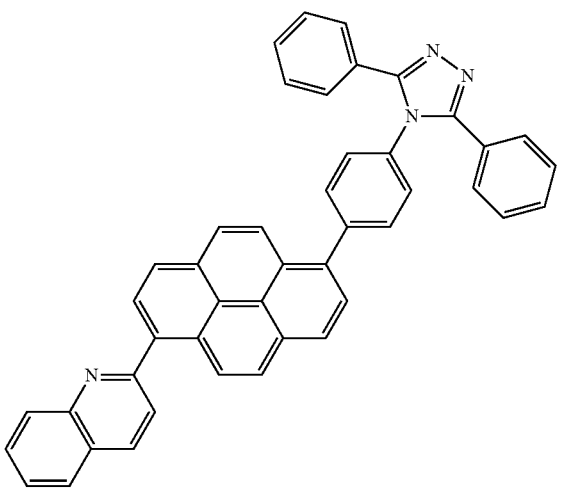
20
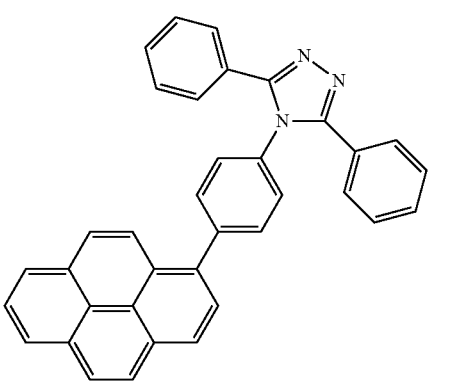

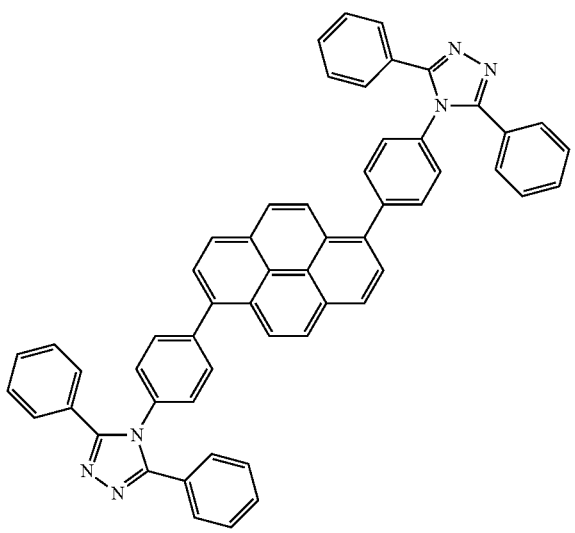

21

The condensed cyclic compound of Formula 1 above may be used as an emitting material, an electron injecting material, and/or an electron transporting material for organic light-emitting devices. The condensed cyclic compound(s) of Formula 1 has a high glass transition temperature (Tg) or a high melting point due to the inclusion of the condensed ring in the molecular structure thereof. Thus, the condensed cyclic compound of Formula 1 above has high heat resistance against Joule's heat generated in an organic layer, between organic layers, or between an organic layer and a metal electrode when light emission occurs, and has high durability in high-temperature environments. An organic light-emitting device manufactured using the condensed cyclic compound of Formula 1 may have improved durability when stored or operated. Although the present invention is not limited by theory and is not limited to the following mechanism, the condensed cyclic compound of Formula 1 above may have a high electron affinity due to the inclusion of an electron transporting nitrogen in a molecular structure, the presence of the electron transporting nitrogen originating from the introduction of a triazole group as a substituent. Accordingly, the condensed cyclic compound of Formula 1 may have improved electron transporting ability and thus may impart a lower driving voltage and improved efficiency to an organic light-emitting device. The condensed cyclic compound of Formula 1 including a pyrene moiety has a larger bandgap as compared with the widely known $Alq_3$ and anthracene compounds and has a low highest occupied molecular orbital (HOMO) energy level due to the inclusion of the triazole group. Therefore, the condensed cyclic compound of Formula 1 may block holes migrating to an electron transport layer from an emission layer, which prevents quenching and contributes to charge balance and thus to long lifetime characteristics of an organic light-emitting device.

As used herein, the unsubstituted $C_1$-$C_{60}$ alkyl group (or a $C_1$-$C_{60}$ alkyl group) may be one of a linear or branched $C_1$-$C_{60}$ alkyl group, including a methyl group, an ethyl group, a propyl group, an isobutyl group, a sec-butyl group, a pentyl group, an iso-amyl group, and a hexyl group. The substituted $C_1$-$C_{60}$ alkyl group refers to the unsubstituted $C_1$-$C_{60}$ alkyl group of which at least one hydrogen atom is substituted with one of a deuterium atom, a halogen atom, a cyano group, a hydroxyl group, a nitro group, an amino group, an amidino group, a silyl group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ an alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group that are substituted with at least one of a deuterium atom, a halogen atom, a cyano group, a hydroxyl group, a nitro group, an amino group, an amidino group, a silyl group, a hydrazine, a hydrazone, a carboxyl group or a salt thereof, a sulfonic acid group or a salt thereof, and a phosphoric acid group or a salt thereof; and a $C_3$-$C_{60}$ cycloalkyl group, a $C_6$-$C_{60}$ aryl group, a $C_2$-$C_{60}$ heteroaryl group, a $C_6$-$C_{60}$ aralkyl group, and a $C_6$-$C_{60}$ aryloxy group that are substituted with at least one of a deuterium atom, a halogen atom, a cyano group, a hydroxyl group, a nitro group, an amino group, an amidino group, a silyl group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{60}$ aryl group, and a $C_2$-$C_{60}$ heteroaryl group.

As used herein, the unsubstituted $C_1$-$C_{60}$ alkoxy group (or a $C_1$-$C_{60}$ alkoxy group) is represented by the formula of —OA (where A is an unsubstituted $C_1$-$C_{60}$ alkyl group as described above). Non-limiting examples of the unsubstituted $C_1$-$C_{60}$ alkoxy group are a methoxy group, an ethoxy group, and an isopropyloxy group. The substituted $C_1$-$C_{60}$ alkoxy group refers to a $C_1$-$C_{60}$ alkoxy group of which at least one hydrogen atom is substituted with those substituents as described above in conjunction with the $C_1$-$C_{60}$ alkyl group.

As used herein, the unsubstituted $C_2$-$C_{60}$ alkenyl group (or a $C_2$-$C_{60}$ alkenyl group) refers to an alkyl group having at least one carbon-carbon double bond in the center or at a terminal of the alkyl group. Examples of the alkenyl group are an ethenyl group, a propenyl group, and a butenyl group. The substituted $C_2$-$C_{60}$ alkenyl group refers to a $C_2$-$C_{60}$ alkenyl group of which at least one hydrogen atom is substituted with those substituents as described above in conjunction with the $C_1$-$C_{60}$ alkyl group.

As used herein, the unsubstituted $C_2$-$C_{60}$ alkynyl group (or a $C_2$-$C_{60}$ alkynyl group) indicates a $C_2$-$C_{60}$ alkyl group having at least one carbon-carbon triple bond in the center or at a terminal of the alkyl group. Non-limiting examples of the unsubstituted $C_2$-$C_{60}$ alkynyl group are an ethynyl group or a propynyl group. The substituted $C_2$-$C_{60}$ alkynyl group refers to a $C_2$-$C_{60}$ alkynyl group of which at least one hydrogen atom is substituted with those substituents as described above in conjunction with the $C_2$-$C_{60}$ alkyl group.

As used herein, the unsubstituted $C_6$-$C_{60}$ aryl group indicates a monovalent $C_2$-$C_{60}$ carbocyclic aromatic system containing at least one aromatic ring. The unsubstituted $C_6$-$C_{60}$ arylene group indicates a divalent $C_6$-$C_{60}$ carbocyclic aromatic system containing at least one aromatic ring When the unsubstituted $C_6$-$C_{60}$ aryl or arylene group includes at least two rings, the at least two rings may be fused to each other. The substituted $C_6$-$C_{60}$ aryl group refers to a $C_6$-$C_{60}$ aryl group of which at least one hydrogen atom is substituted with those substituents as described above in conjunction with the $C_1$-$C_{60}$ alkyl group. The substituted $C_6$-$C_{60}$ arylene group refers to a $C_6$-$C_{60}$ arylene group of which at least one hydrogen atom is substituted with those substituents as described above in conjunction with the $C_1$-$C_{60}$ alkyl group.

Non-limiting examples of the substituted or unsubstituted $C_6$-$C_{60}$ aryl group are a phenyl group, a $C_1$-$C_{10}$ alkylphenyl group (for example, an ethylphenyl group), a $C_1$-$C_{10}$ alkylbiphenyl group (for example, an ethylbiphenyl group), a halophenyl group (for example, o-, m- and p-fluorophenyl group, a dichlorophenyl group), a dicyanophenyl group, a trifluoromethoxyphenyl group, o-, m-, and p-tolyl group, o-, m- and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

Examples of the substituted $C_6$-$C_{60}$ aryl group may be inferred based on the above-described examples of the unsubstituted $C_6$-$C_{60}$ aryl group and substituted $C_1$-$C_{60}$ alkyl group. Examples of the substituted or unsubstituted $C_6$-$C_{60}$ arylene group may be inferred based on the above-described examples of the substituted or unsubstituted $C_6$-$C_{60}$ aryl group.

The unsubstituted $C_2$-$C_{60}$ heteroaryl group is a monovalent carbocyclic aromatic system having at least one aromatic ring and at least one of the heteroatoms selected from the group consisting of N, O, P, and S. The unsubstituted $C_2$-$C_{60}$ heteroarylene group is a divalent carbocyclic aromatic system having at least one aromatic ring and at least one of the heteroatoms selected from N, O, P, and S. In this regard, when the heteroaryl group and the heteroarylene group have at least two rings, they may be fused to each other. The substituted $C_2$-$C_{60}$ heteroaryl group refers to a $C_2$-$C_{60}$ heteroaryl group of which at least one hydrogen atom is substituted with those substituents as described above in conjunction with the $C_1$-$C_{60}$ alkyl group. The substituted $C_2$-$C_{60}$ heteroarylene group refers to a $C_2$-$C_{60}$ heteroarylene group of which at least one hydrogen atom is substituted with those substituents as described above in conjunction with the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the substituted $C_2$-$C_{60}$ heteroaryl group may be referred based on the above-described exemplary substitutents of the unsubstituted $C_2$-$C_{60}$ heteroaryl group and substituted $C_1$-$C_{60}$ alkyl group. Examples of the substituted or unsubstituted $C_2$-$C_{60}$ heteroarylene group may be inferred based on the above-described exemplary substituents of the substituted or unsubstituted $C_2$-$C_{60}$ heteroaryl group described above.

The substituted or unsubstituted $C_6$-$C_{60}$ aryloxy group indicates —$OA_2$ (where $A_2$ is a substituted or unsubstituted $C_6$-$C_{60}$ aryl group as described above). The substituted or unsubstituted $C_6$-$C_{60}$ arylthiol group indicates —$SA_3$ (where $A_3$ is a substituted or unsubstituted $C_6$-$C_{60}$ aryl group as described above).

The condensed cyclic compound of Formula 1 may be synthesized by using organic synthesis. A synthesis method of the fused ring compound of Formula 1 may be understood by those of ordinary skill in the art from the examples that will be described below.

The condensed cyclic compound of Formula 1 may be used between a pair of electrodes of an organic light-emitting device. For example, the fused ring compound may be used in an emission layer, in a layer between the anode and the emission layer (for example, a hole injection layer, a hole transport layer, or a functional layer with both hole injection and transport capabilities), and/or in a layer between the cathode and the emission layer (for example, an electron injection layer, an electron transport layer, or a functional layer with both electron injection and transport capabilities).

According to another embodiment of the present invention, an organic light-emitting device includes a first electrode, a second electrode disposed opposite to the first electrode, and an organic layer disposed between the first electrode and the second electrode, the organic layer including at least one of the condensed cyclic compounds of Formula 1 described above.

As used herein, the term "organic layer" refers to a layer containing an organic compound and including at least one layer. For example, the organic layer may include at least one layer selected from a hole injection layer, a hole transport layer, a functional layer (hereinafter, "hole injection and transport layer") having both hole injection and hole transport capabilities, an electron blocking layer, an emission layer, a hole blocking layer, an electron injection layer, an electron transport layer, and a functional layer (hereinafter, "electron injection and transport layer") having both electron injection and electron transport capabilities.

The organic layer may not include solely an organic compound. The organic layer may include an inorganic compound or an inorganic material. In one embodiment, the organic layer may include both an organic compound and an inorganic compound or an inorganic material in one layer. For example, the organic layer may include an organometallic complex in one layer. In another embodiment, the organic layer may include a layer containing an organic compound and a layer containing an inorganic compound or an inorganic material.

The organic layer may include at least one of the condensed cyclic compounds listed above in one layer, and, in some other embodiments, may include at least one of the condensed cyclic compounds listed above in layers. For example, the organic layer may include one of the condensed cyclic compounds of Formula 1 above as a dopant in an emission layer and another condensed cyclic compound of Formula 1 as an electron transport material in an electron transport layer. In another embodiment, the organic layer may include one of the condensed cyclic compounds of Formula 1 as an emitting dopant and another condensed cyclic compound as a host in an emission layer. In another embodiment, the organic layer may include one of the condensed cyclic compounds as an emitting dopant and another condensed cyclic compound as an host in an emission layer, and still another condensed cyclic compound as an electron transport material in an electron transport layer.

The organic layer may include at least one of an emission layer, an electron injection layer, an electron transport layer, and an electron injection and transport layer, and at least one of the emission layer, the electron injection layer, the electron transport layer, and the electron injection and transport layer may include the condensed cyclic compound of Formula 1.

For example, the organic layer may include an emission layer, the emission layer including a host and a dopant, and the condensed cyclic compound of Formula 1 may serve as a fluorescent host or a phosphorescent host of the emission layer.

The emission layer may include a host and a dopant, the emission layer further including one of a fluorescent dopant and a phosphorescent dopant. For example, the phosphorescent dopant may be, but is not limited to, an organometallic complex including at least one of iridium (Ir), platinum (Pt), osmium (Os), rhenium (Re), titanium (Ti), zirconium (Zr), hafnium (Hf), europium (Eu), terbium (Tb), and thulium (Tm). The emission layer may or may not include the condensed cyclic compound of Formula 1 above.

The organic layer may include at least one of the hole injection layer, the hole transport layer, and the hole injection and transport layer, and at least one of these layers may further include a charge generating material. The charge generating material may be, for example, a p-dopant.

FIG. 1 is a schematic sectional view of an organic light-emitting device 10 according to an embodiment of the present invention. Hereinafter, a structure of an organic light-emitting device according to an embodiment of the present invention and a method of manufacturing the same will now be described with reference to FIG. 1.

Referring to FIG. 1, the organic light-emitting device 10 includes a first electrode 13, an organic layer 15, and a second electrode 17, which are sequentially stacked on a substrate 11 in this order.

The substrate 11 may be any substrate that is used in existing organic light-emitting devices. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transmission electrode. Transparent and conductive materials such as indium tin oxide (ITO), indium zinc oxide (IZO), $SnO_2$, and ZnO may be used as materials for the first electrode 13. In some embodiments, the first electrode 13 may be formed as a reflective electrode using one of magnesium (Mg), silver (Ag), aluminum (Al), aluminum-lithium (Al—Li), calcium (Ca), magnesium-indium (Mg—In), magnesium-silver (Mg—Ag), and the like. The first electrode 13 may have a single-layer structure or a multi-layer structure including at least two layers. For example, the first electrode 13 may have a three-layered structure of ITO/Ag/ITO, but it is not limited thereto.

The organic layer 15 may be disposed on the first electrode 13.

The organic layer 15 may include a hole injection layer (HIL), a hole transport layer (HTL), an emission layer (EML), an electron transport layer (ETL), and an electron injection layer (EIL).

The HIL may be formed on the first electrode 13 by one of vacuum deposition, spin coating, casting, Langmuir-Blodgett (LB) deposition, and the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL and the desired structure and thermal properties of the HIL to be formed. For example, the spin rate may be in the range of about 2000 rpm to about 5000 rpm, and a temperature at which heat treatment is performed to remove a solvent after coating may be in the range of about 80° C. to about 200° C. However, the coating conditions are not limited thereto.

For example, as a HIL material, any hole injection material may be used. Non-limiting examples of hole injection materials are N,N'-diphenyl-N,N'-bis-[4-(phenyl-m-tolylamino)-phenyl]-biphenyl-4,4'-diamine, (DNTPD), a phthalocyanine compound such as copper phthalocyanine, 4,4',4"-tris(3-methylphenylphenylamino)triphenylamine (m-MTDATA), 4,4',4"-tris(N,N-diphenylamino)triphenylamine (TDATA), 4,4',4"-tris[N,-(2-naphthyl)-N-phenylamino]-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), and polyaniline)/poly(4-styrenesulfonate (PANI/PSS).

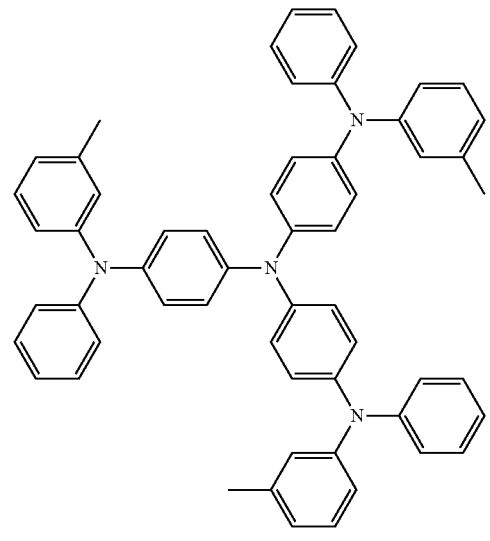

m-MTDATA

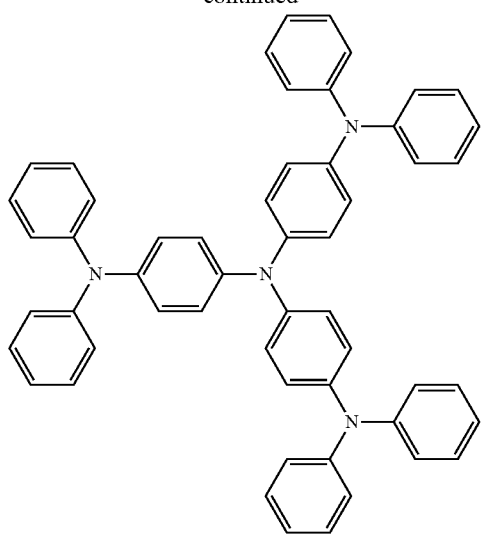

TDATA

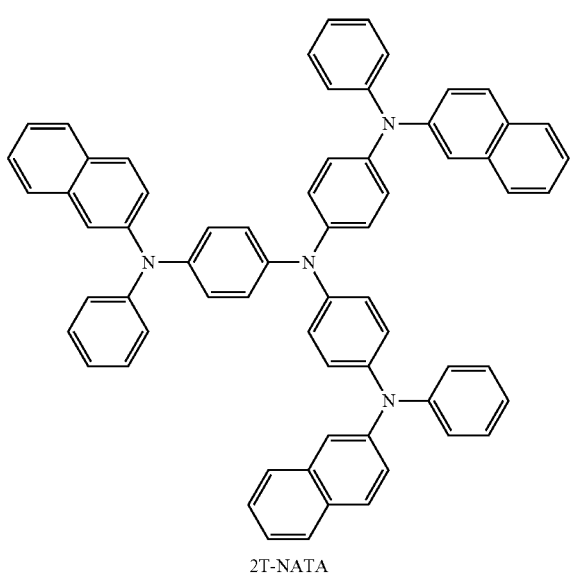

2T-NATA

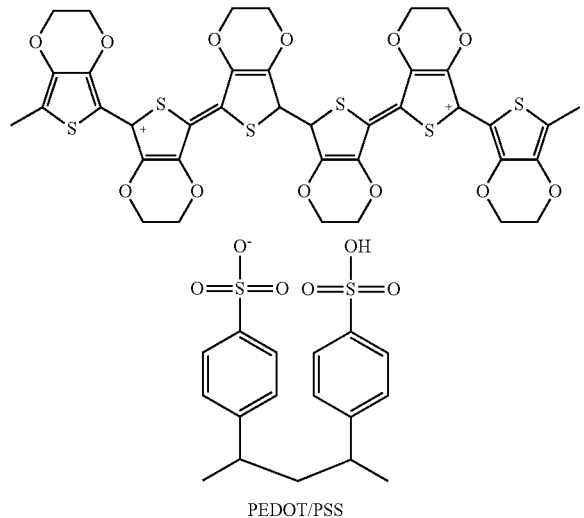

PEDOT/PSS

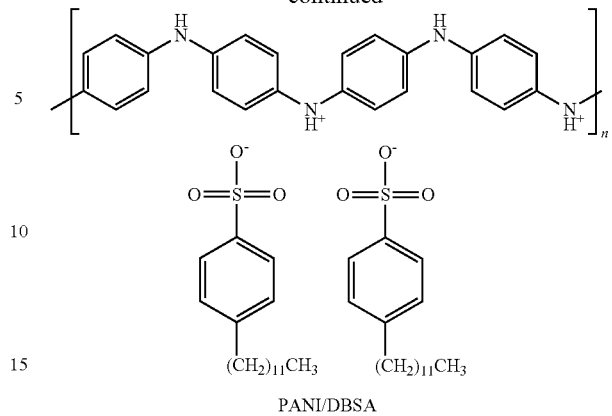

PANI/DBSA

The thickness of the HIL may be about 100 Å to about 10,000 Å, and, in some embodiments, may be from about 100 Å to about 1,000 Å. When the thickness of the HIL is within these ranges, the HIL may have good hole injecting ability without imparting a substantial increase in driving voltage to an OLED including it.

Then, a HTL may be formed on the HIL by using one of vacuum deposition, spin coating, casting, Langmuir-Blodgett (LB) deposition, and the like. When the HTL is formed using one of vacuum deposition and spin coating, the conditions for deposition and coating may be similar to those for the formation of the HIL, though the conditions for the deposition and coating may vary according to the material that is used to form the HTL.

The HTL may be formed of any hole-transporting materials. Non-limiting examples of hole transporting materials are carbazole derivatives, such as one of N-phenylcarbazole, polyvinylcarbazole, and the like; TPD (N,N'-bis(3-methylphenyl)-N,N'-diphenyl-[1,1-biphenyl]-4,4'-diamine); NPB (N,N'-di(1-naphthyl)-N,N-diphenylbenzidine), α-NPD (N,N-bis(naphthalen-1-yl)-N,N-bis(phenyl)-2,2'-dimethylbenzidine, and TCTA (4,4',4"-tris(N-carbazolyl)triphenylamine).

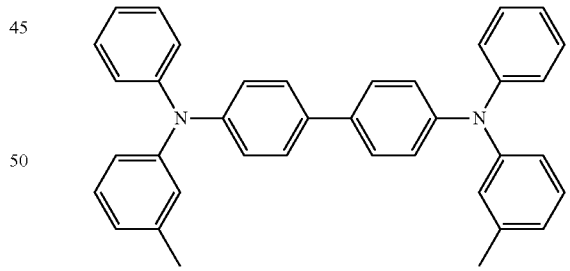

TPD

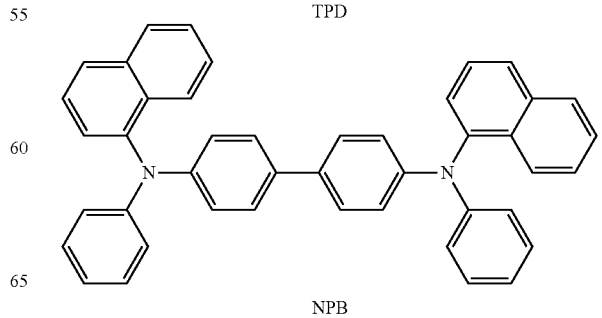

NPB

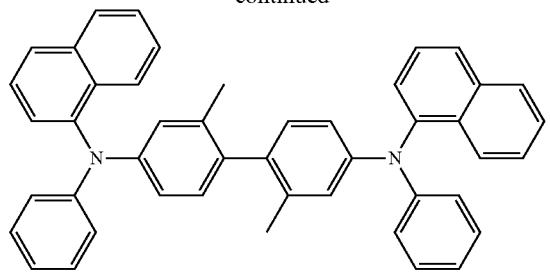

α-NPD

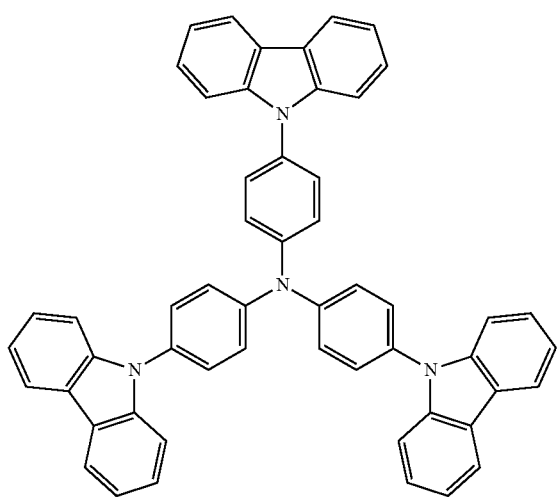

TCTA

The thickness of the HTL may be from about 50 Å to about 1,000 Å, and, in some embodiments, from about 100 Å to about 800 Å. When the thickness of the HTL 14 is within these ranges, the HTL 140 may have satisfactory hole transporting ability without imparting a substantial increase in driving voltage to an OLED including it.

In some embodiments, instead of the HIL and the HTL, a hole injection and transport layer may be formed. The hole injection and transport layer may include at least one of the hole injection layer materials and hole transport layer materials described above. A thickness of the hole injection and transport layer may be from about 500 Å to about 10,000 Å, and, in some embodiments, may be from about 100 Å to about 1,000 Å. When the thickness of the hole injection and transport layer is within these ranges, the hole injection and transport layer may have good hole injection and transport capabilities without imparting a substantial increase in driving voltage to an OLED including it.

In some embodiments, at least one of the HIL, HTL, and hole injection and transport layer may include at least one of a compound of Formula 100 below and a compound of Formula 101 below:

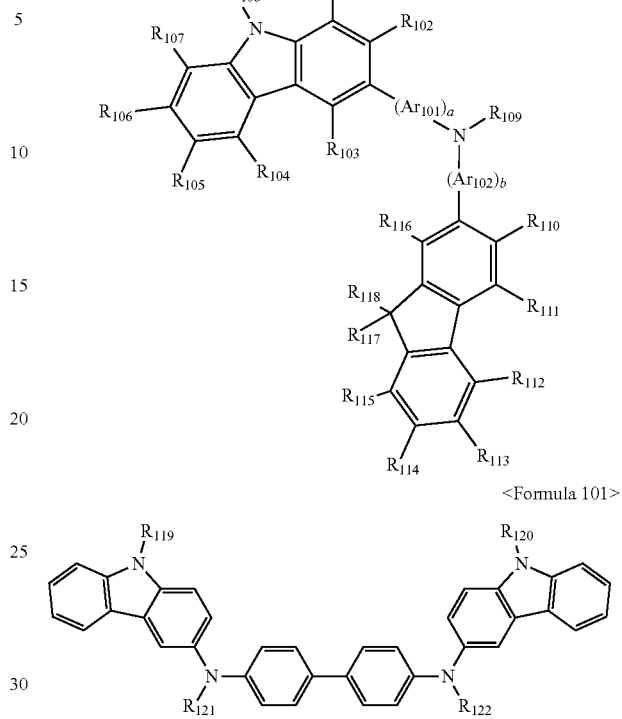

In Formula 100, $Ar_{101}$ and $Ar_{102}$ may be each independently one of a substituted or unsubstituted $C_6$-$C_{40}$ arylene group. In some embodiments, $Ar_{101}$ and $Ar_{102}$ may be each independently one of a phenylene group, a pentalenylene group, an indenylene group, a naphthylene group, an azulenylene group, a heptalenylene group, a substituted or unsubstituted acenaphthylene group, a fluorenylene group, a pentalenylene group, a phenanthrenylene group, an anthrylene group, a fluoranthenylene group, a triphenylenylene group, a pyrenylene group, a chrysenylene group, a naphthacenylene group, a picenylene group, a perylenylene group, and a pentacenylene group; and a phenylene group, a pentalenylene group, an indenylene group, a naphthylene group, an azulenylene group, a heptalenylene group, a substituted or unsubstituted acenaphthylene group, a fluorenylene group, a pentalenylene group, a phenanthrenylene group, an anthrylene group, a fluoranthenylene group, a triphenylenylene group, a pyrenylene group, a chrysenylene group, a naphthacenylene group, a picenylene group, a perylenylene group, and a pentacenylene group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{40}$ alkyl group, a $C_2$-$C_{40}$ alkenyl group, a $C_2$-$C_{40}$ alkynyl group, a $C_1$-$C_{40}$ alkoxy group, a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{40}$ aryl group, a $C_6$-$C_{40}$ aryloxy group, a $C_6$-$C_{40}$ arylthio group, and a $C_2$-$C_{40}$ heteroaryl group.

In Formula 100, a and b may be each independently an integer from 0 to 5, for example, 0, 1, or 2. For example, a may be 1, and b may be 0, but the assignment of a and b is not limited thereto.

In Formulae 100 and 101, $R_{101}$ to $R_{122}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{40}$ alkyl group, a substituted or unsubstituted $C_2$-$C_{40}$ alkenyl group, a substituted or unsubstituted $C_2$-$C_{40}$ alkynyl group, a substituted or unsubstituted $C_1$-$C_{40}$ alkoxy group, a substituted or unsubstituted $C_3$-$C_{40}$ cycloalkyl group, a substituted or unsubstituted $C_6$-$C_{40}$ aryl group, a substituted or unsubstituted $C_6$-$C_{40}$ aryloxy group and a substituted or unsubstituted $C_6$-$C_{40}$ arylthio group.

In some other embodiments, $R_{101}$ to $R_{108}$, and $R_{110}$ to $R_{122}$ may be each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group (for example, one of a methyl group, an ethyl group, a propyl group, a butyl group, a pentyl group, a hexyl group, and the like), a $C_1$-$C_{10}$ alkoxy group (for example, one of a methoxy group, an ethoxy group, a propoxy group, a butoxy group, a pentoxy group, and the like), a phenyl group, a naphthyl group, an anthryl group, a fluorenyl group, a pyrenyl group; and a $C_1$-$C_{10}$ alkyl group, a $C_1$-$C_{10}$ alkoxy group, a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof, but embodiments of the invention are not limited thereto.

In Formula 100, $R_{109}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment, the compound of Formula 100 may be a compound represented by Formula 100A below, but it is not limited thereto:

<Formula 100A>

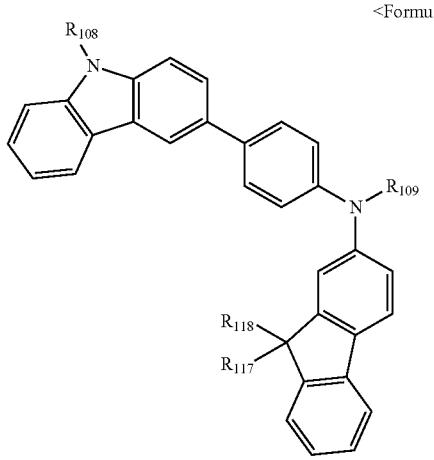

In Formula 100A, $R_{108}$, $R_{109}$, $R_{117}$, and $R_{118}$ may be as defined above.

In some embodiments, at least one of the HIL, HTL, and hole injection and transport layer may include at least one of compounds represented by Formulae 102 to 121 below, but it is not limited thereto:

102

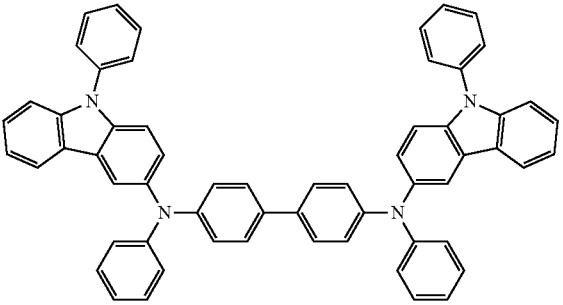

103

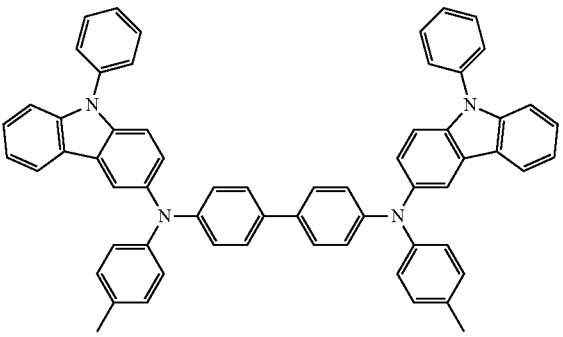

104

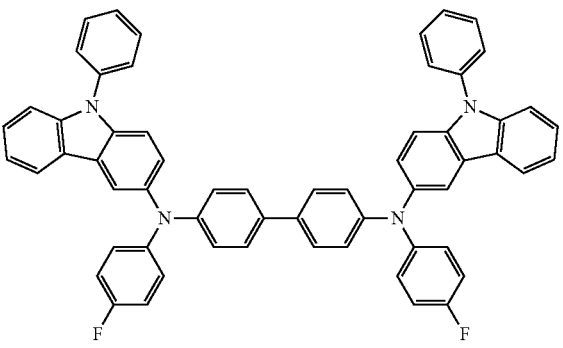

105

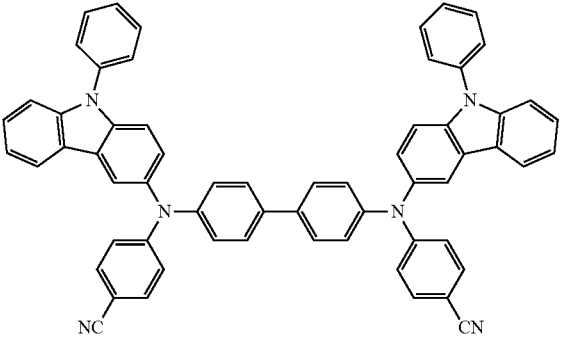

106
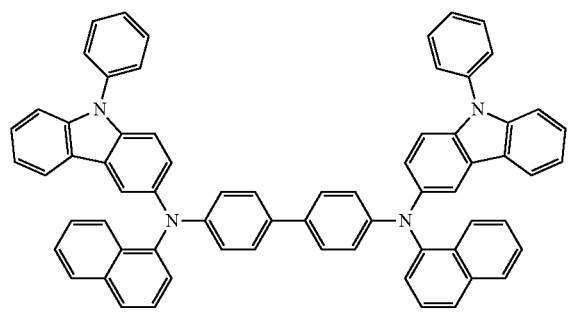
107
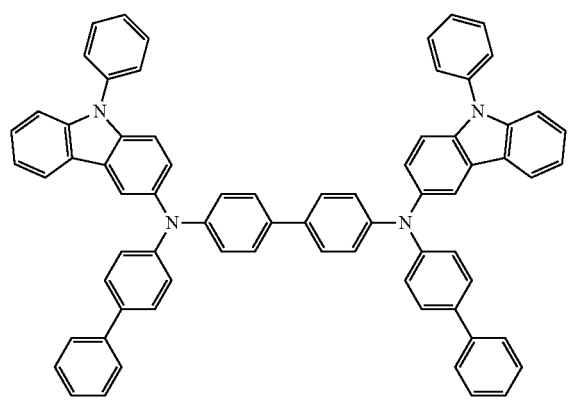
108
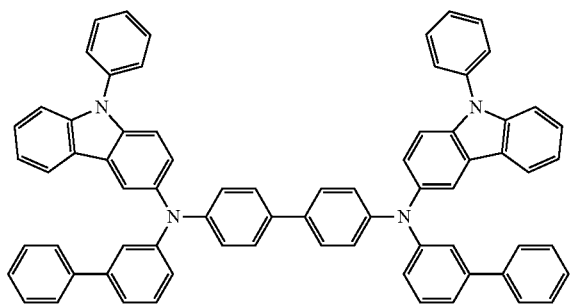
109
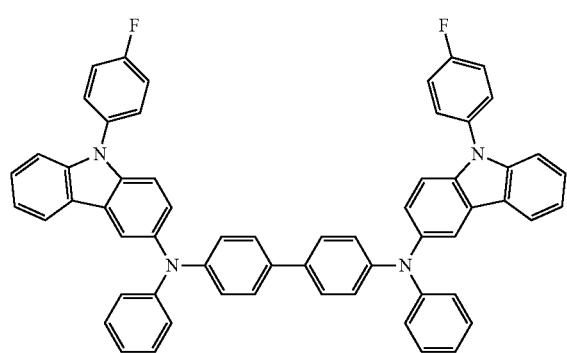
110
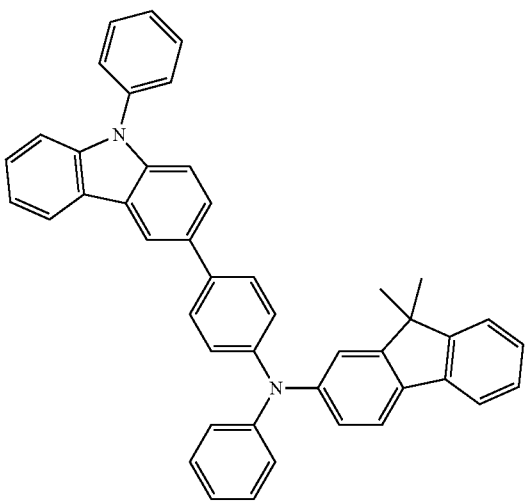
111
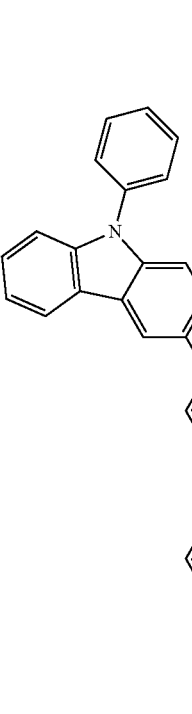

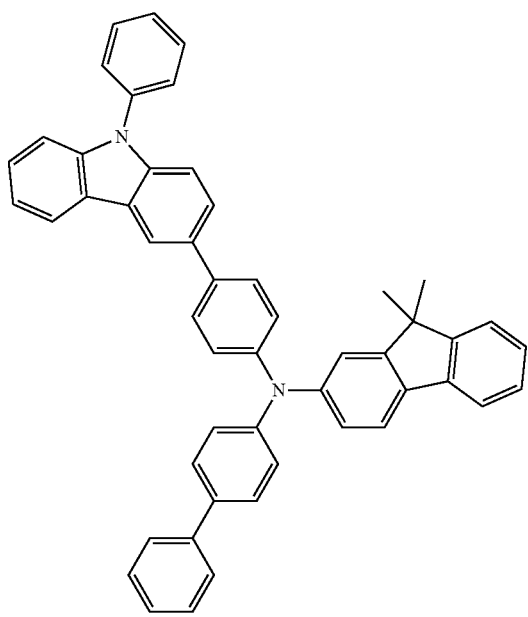
112
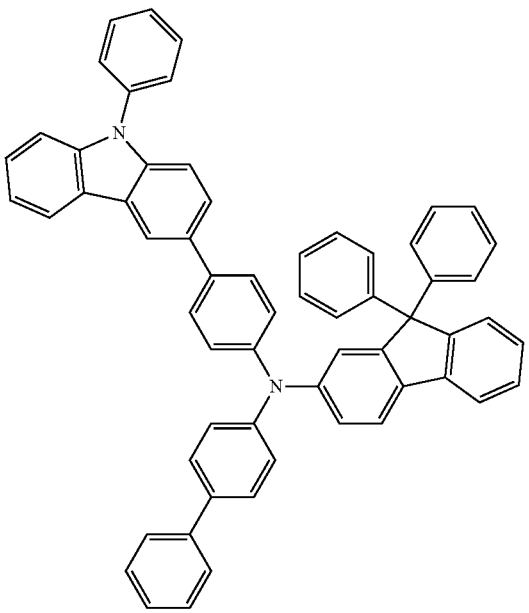
114
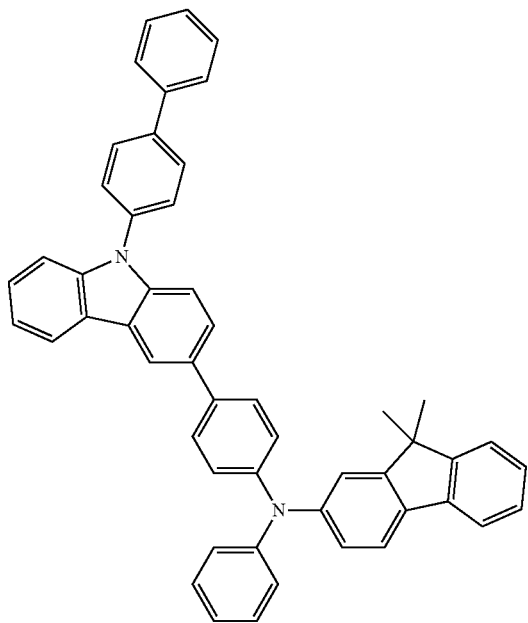
113
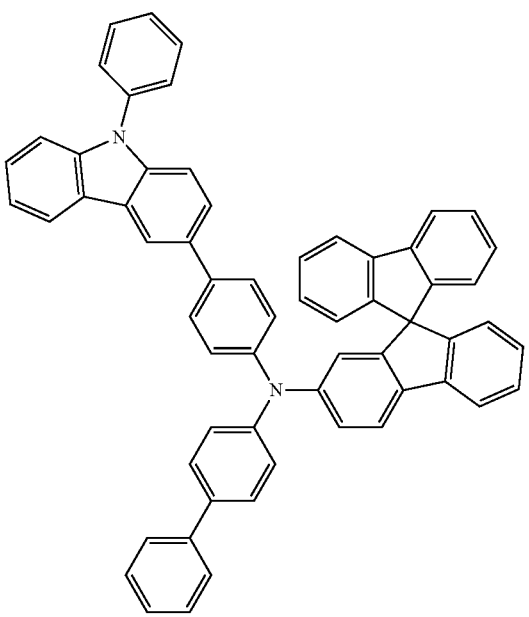
115

116
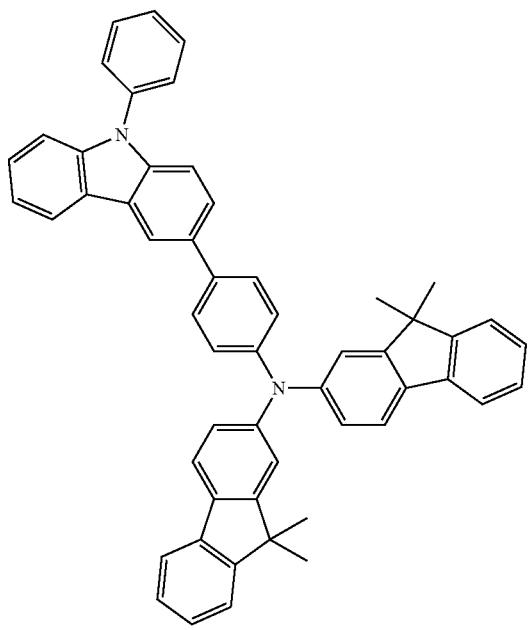
117
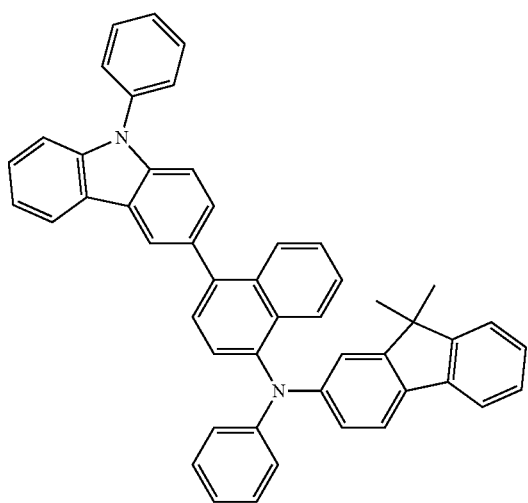
118
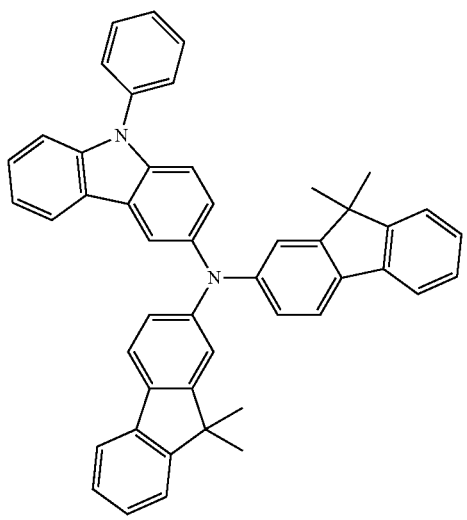
119
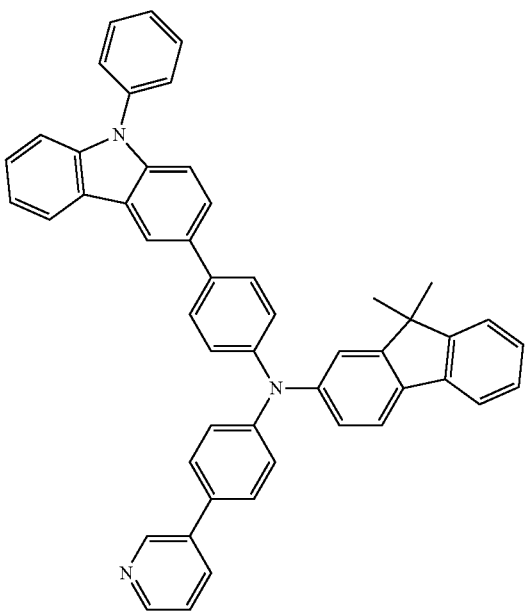

120

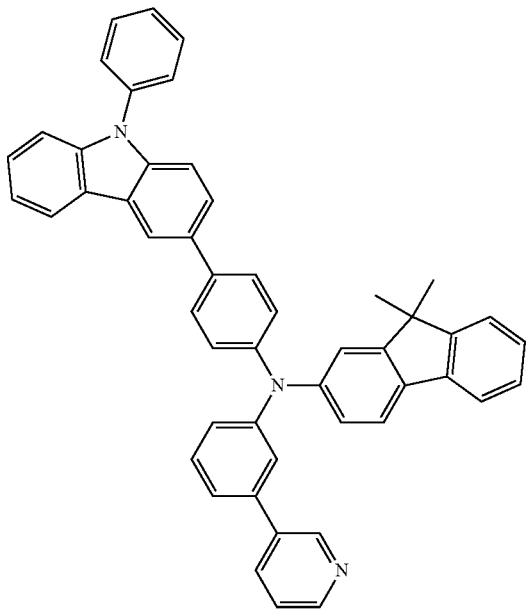

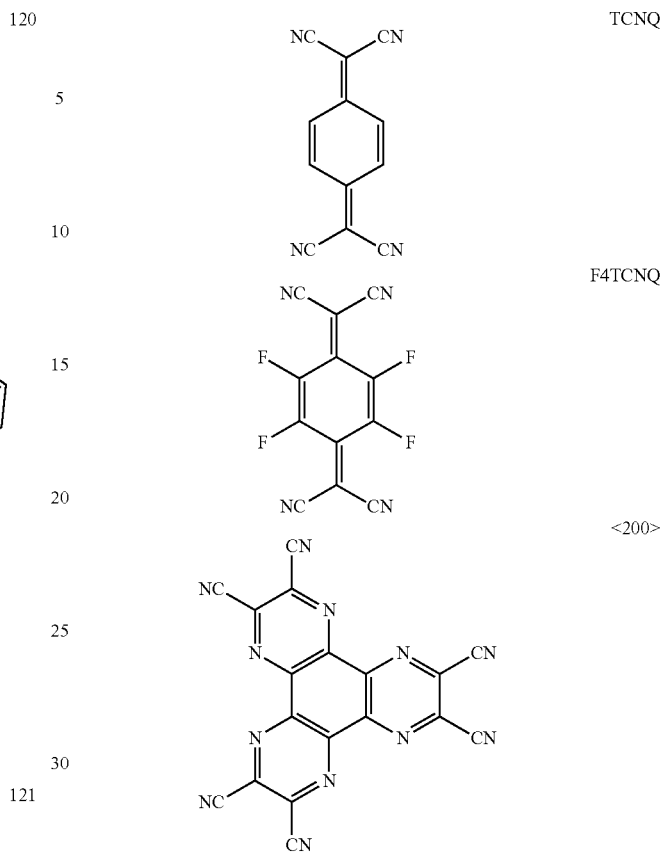

TCNQ

F4TCNQ

<200>

121

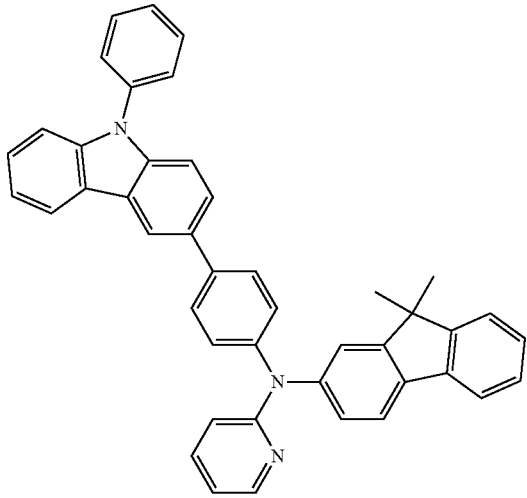

At least one of the HIL, HTL, and hole injection and transport layer may further include a charge-generating material for improved layer conductivity, in addition to a known hole injecting material, hole transport material, and/ or material having both hole injection and hole transport capabilities as described above.

The charge-generating material may be, for example, a p-dopant. Non-limiting examples of the p-dopant are quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 200 below.

When the hole injection layer, the hole transport layer, or the hole injection and transport layer further includes a charge generating material, the charge generating material may be, but is not limited to, one of homogeneously dispersed and inhomogeneously distributed in the layer.

A buffer layer may be disposed between at least one of the HIL, HTL and hole injection and transport layer, and the EML. The buffer layer may compensate for an optical resonance distance of light according to a wavelength of the light emitted from the EML, and thus may increase efficiency. The buffer layer may include any hole injecting material or hole transporting material. In some other embodiments, the buffer layer may include the same material as one of the materials included in the HIL, HTL, and hole injection and transport layer.

Then, an EML may be formed on one of the HTL, hole injection and transport layer, and buffer layer by one of vacuum deposition, spin coating, casting, Langmuir-Blodget (LB) deposition, and the like. When the EML is formed using one of vacuum deposition and spin coating, the deposition and coating conditions may be similar to those for the formation of the HIL, though the conditions for deposition and coating may vary according to the material that is used to form the EML.

The EML may be formed using at least one of the condensed cyclic compounds of Formula 1 above and known light-emitting materials (including hosts and dopants). When including the condensed cyclic compound of Formula 1 above, the EML may further include at least one of a known phosphorescent host, a fluorescent host, a phosphorescent dopant and a fluorescent dopant, in addition to the condensed cyclic compound of Formula 1 above. The condensed cyclic compound of Formula 1 above may serve as one of a fluorescent host and a phosphorescent host.

The condensed cyclic compound of Formula 1 above may be used as a host. In another embodiment, a widely-known host may be used. Non-limiting examples of known hosts are Alq$_3$ (tris(8-quinolinorato)aluminum), CBP (4,4'-N,N'-dicabazole-biphenyl), PVK (poly(n-vinylcarbazole), ADN (9,10-di(naphthalene-2-yl)anthracene), TCTA, TPBI ((1,3,5-tris(N-phenylbenzimidazole-2-yl)benzene), TBADN ((3-tert-butyl-9,10-di(naphth-2-yl) anthracene), DSA (distyrylarylene), E3 (2,7-bis(9,9-diethylfluoren-2-yl)-9,9-diethylfluorene), dmCBP (2,2'-dimethyl-4,4'-bis(N-carbazolyl)biphenyl), and Compounds 301 to 309 below.

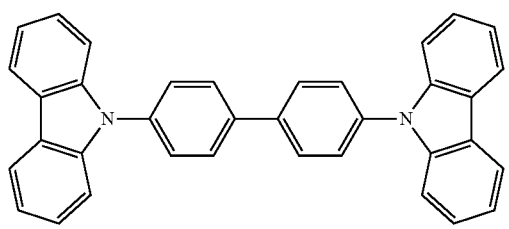

CBP

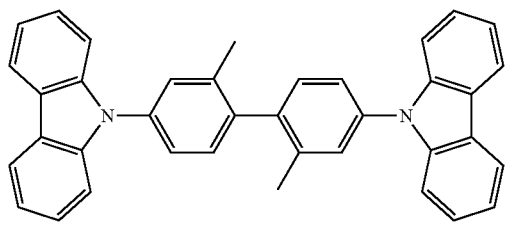

dmCBP

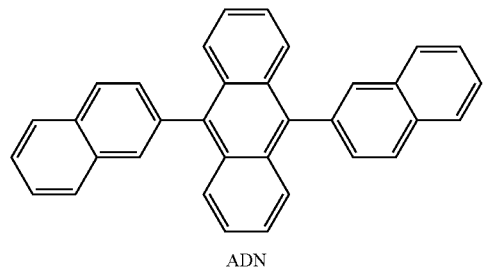

ADN

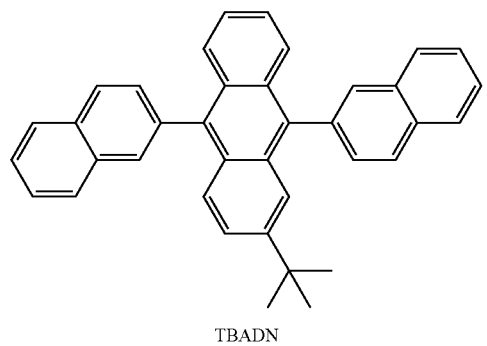

TBADN

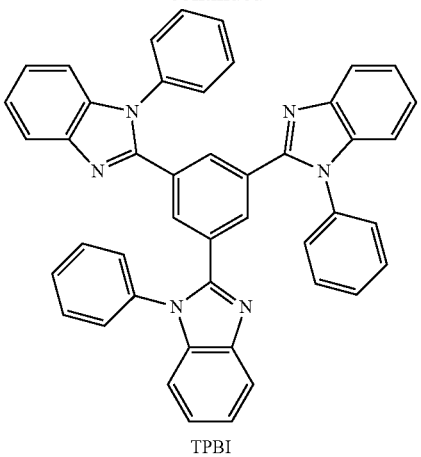

TPBI

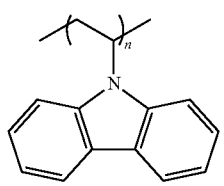

PVK

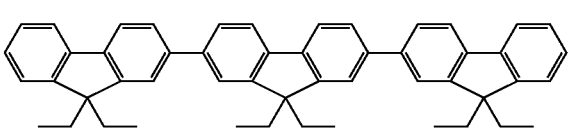

E3

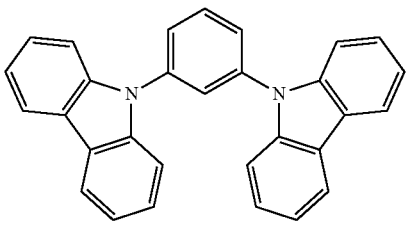

301

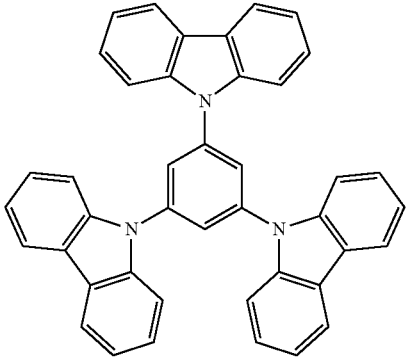

302

-continued
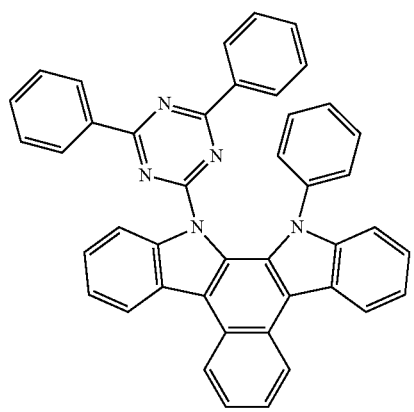
303
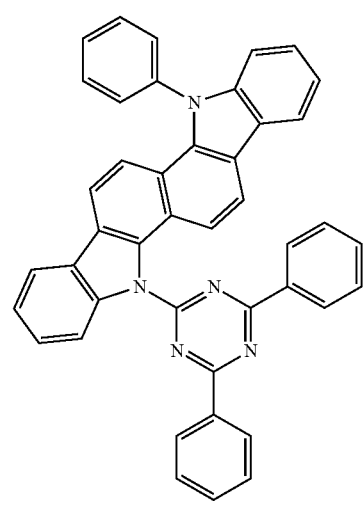
304
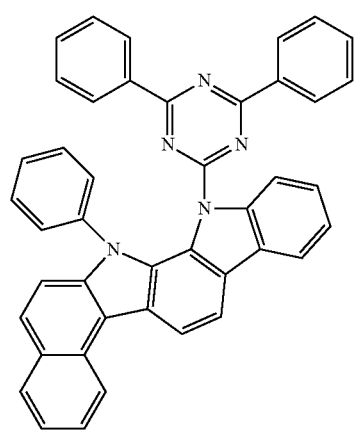
305
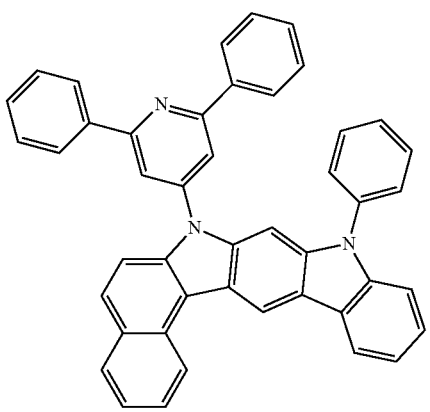
306
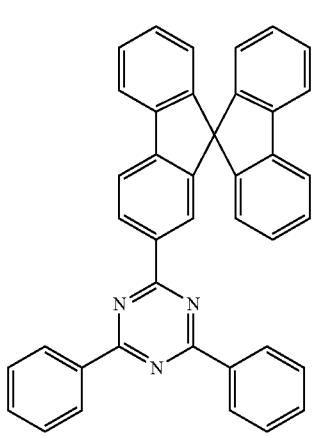
307
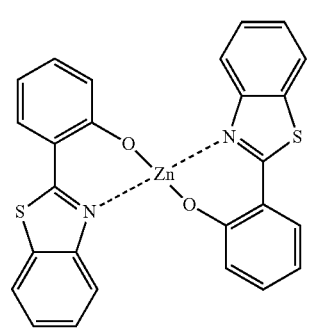
308
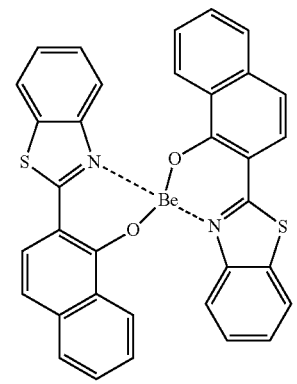
309

In some embodiments, an anthracene-based compound represented by Formula 400 below may be used as the host.

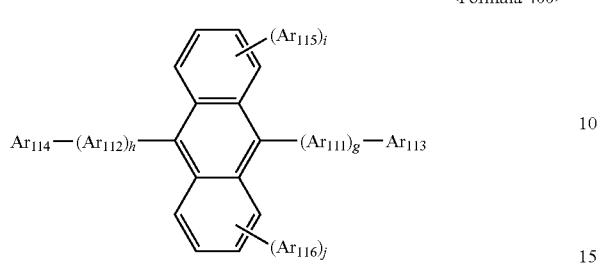

<Formula 400>

In Formula 400, $Ar_{111}$ and $Ar_{112}$ may be each independently a substituted or unsubstituted $C_6$-$C_{60}$ arylene group; $Ar_{113}$ to $Ar_{116}$ may be each independently one of a substituted or unsubstituted $C_1$-$C_{10}$ alkyl group and a substituted or unsubstituted $C_6$-$C_{60}$ aryl group; and g, h, i, and j may be each independently an integer from 0 to 4.

In some embodiments, $Ar_{111}$ and $Ar_{112}$ in Formula 400 may be each independently one of a phenylene group, a naphthylene group, a phenanthrenylene group, and a pyrenylene group; one of a phenylene group, a naphthylene group, a phenanthrenylene group, a fluorenyl group, and a pyrenylene group that is substituted with at least one of a phenyl group, a naphthyl group, and an anthryl group.

In Formula 400 above, g, h, i, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, a fluorenyl group, and

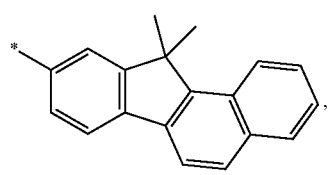 [SMILES: *c1ccc2c(c1)C(C)(C)c1c-2ccc2ccccc12]

but they are not limited thereto.

For example, the anthracene-based compound of Formula 400 above may be one of the compounds represented by the following formulae, but it is not limited thereto:

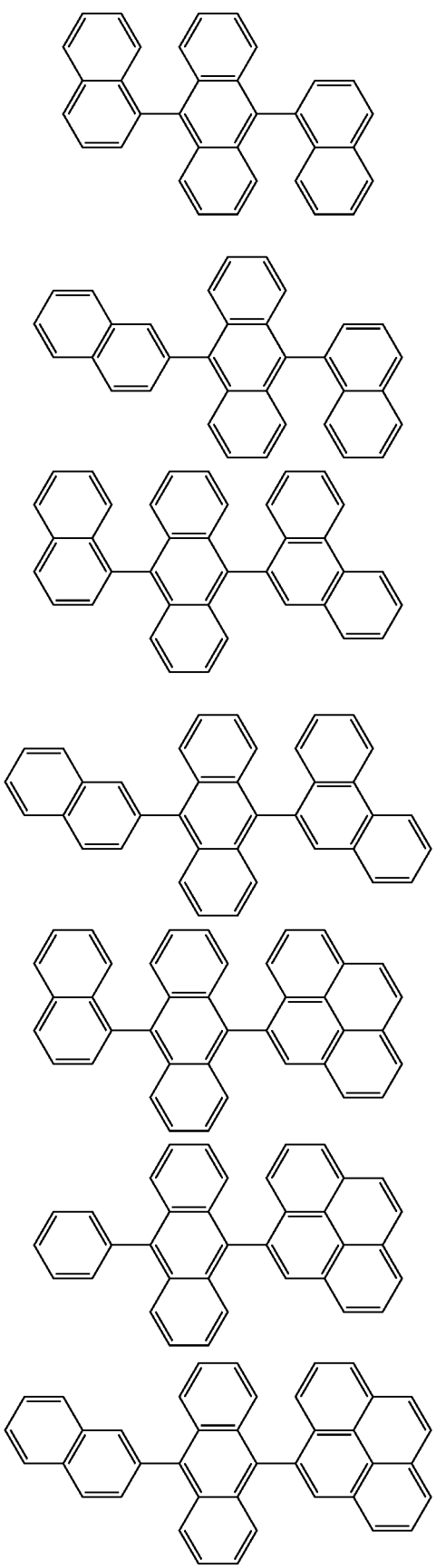

-continued
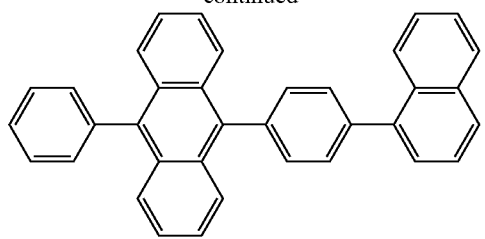
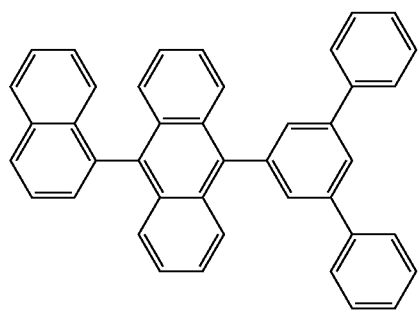
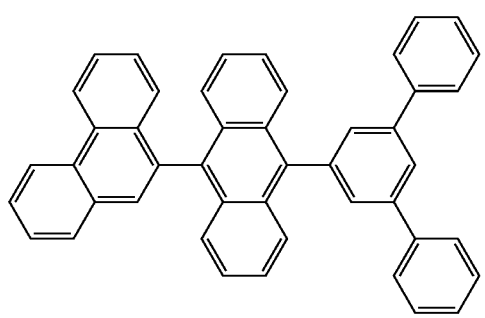
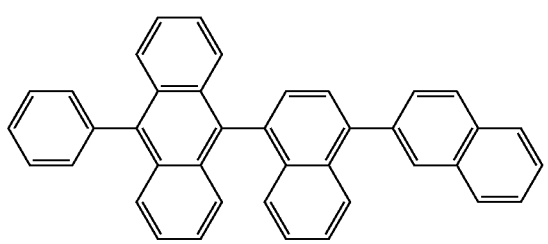
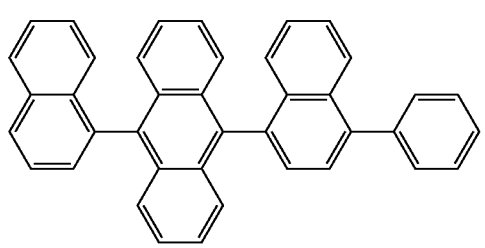
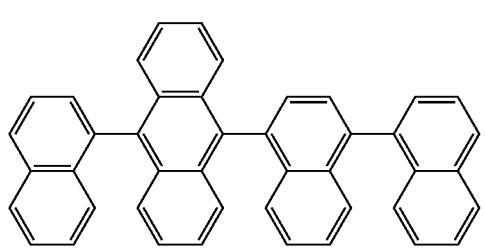
-continued
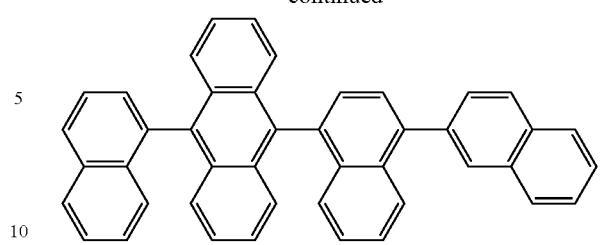
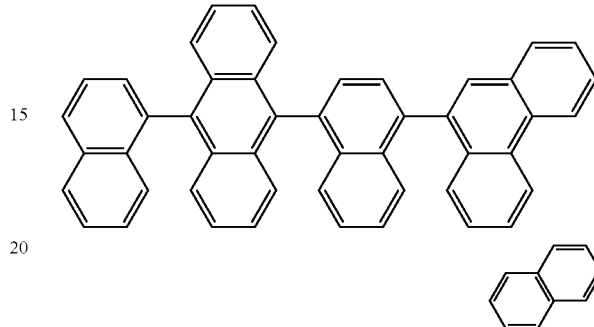
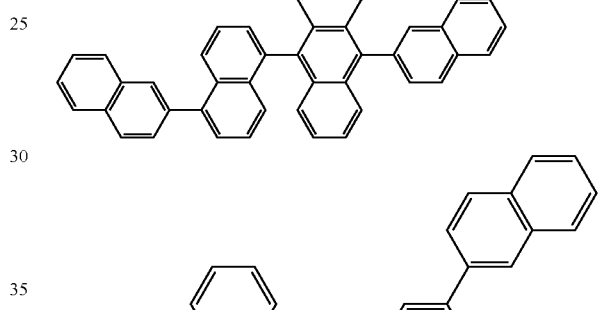
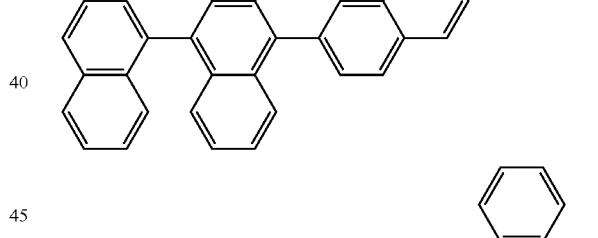
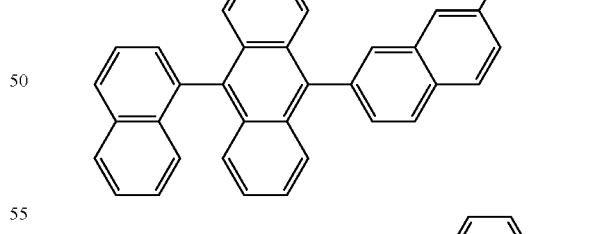
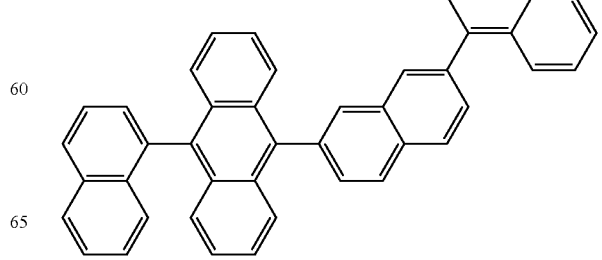

-continued
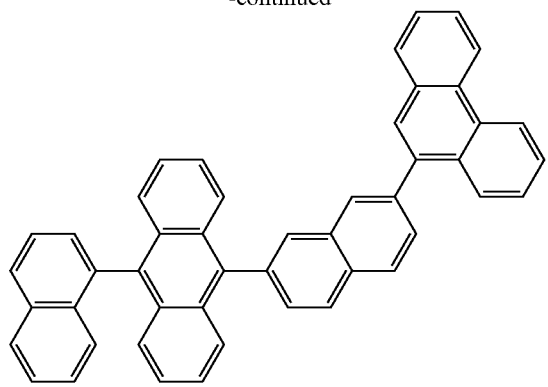
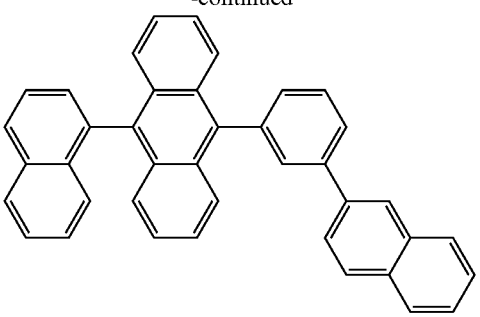
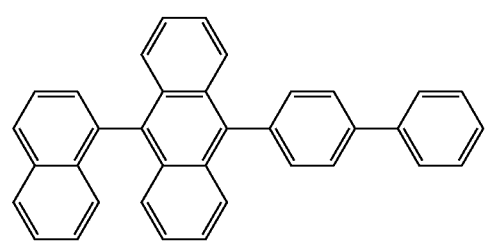
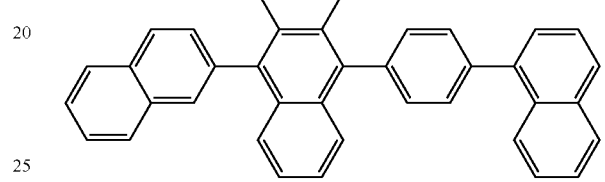
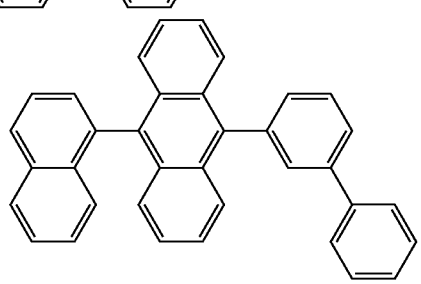
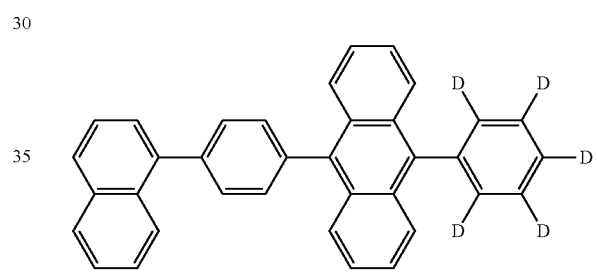
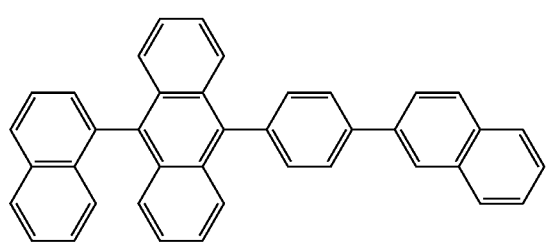
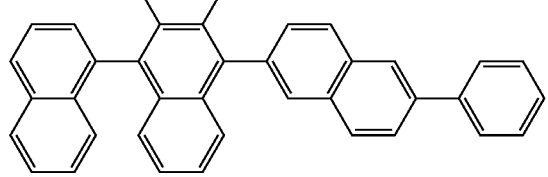
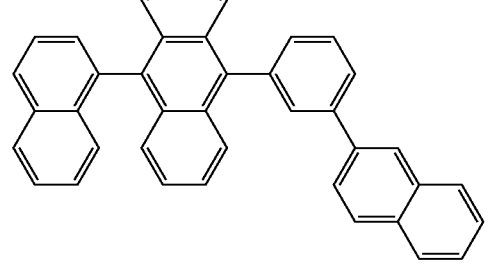
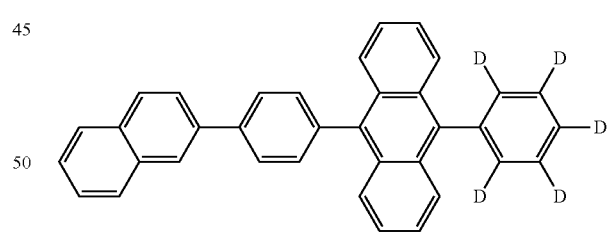
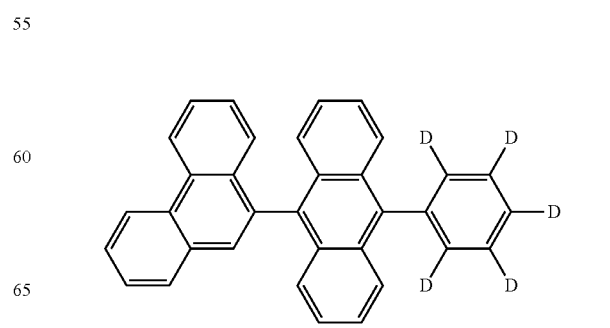

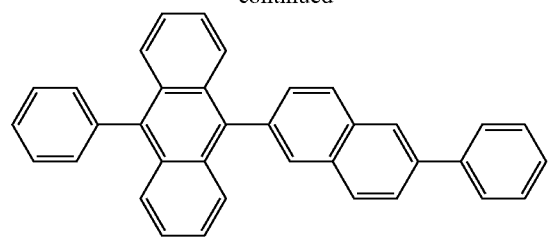
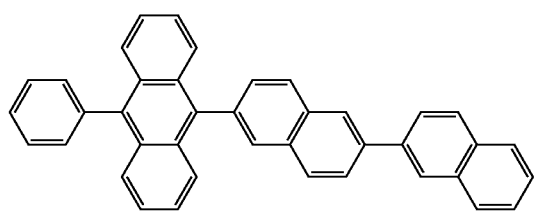
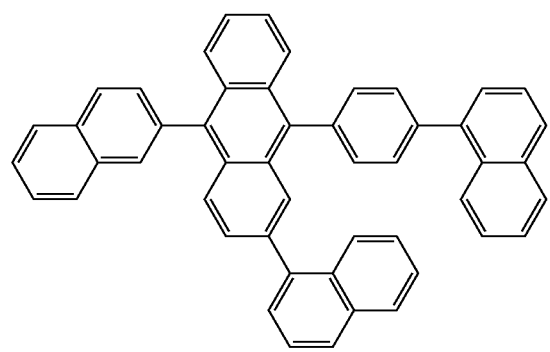
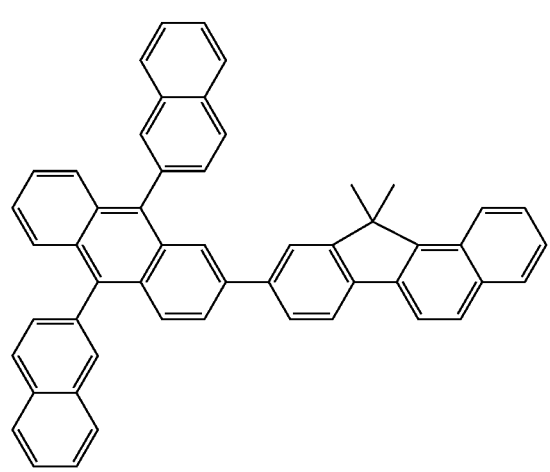
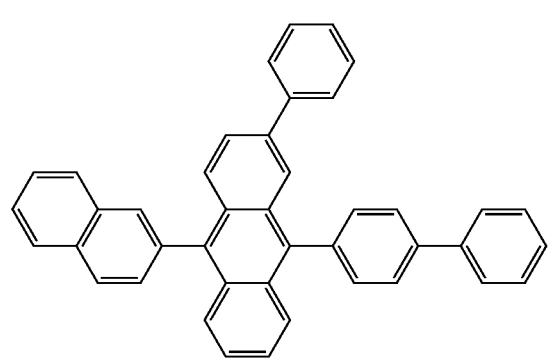
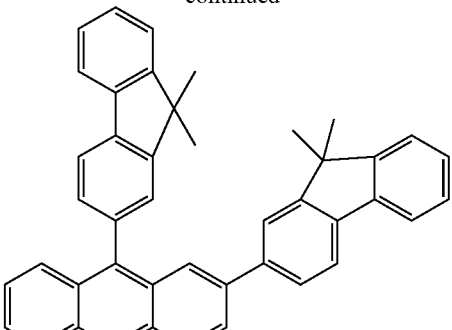
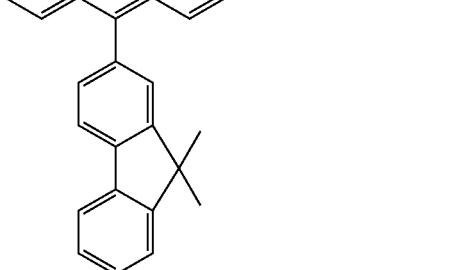
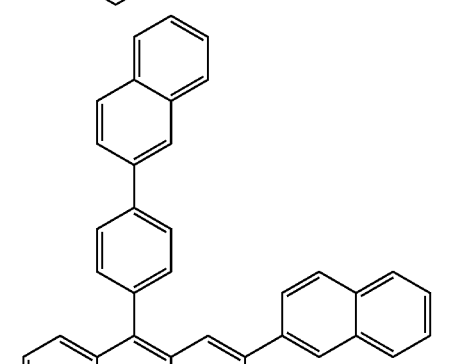
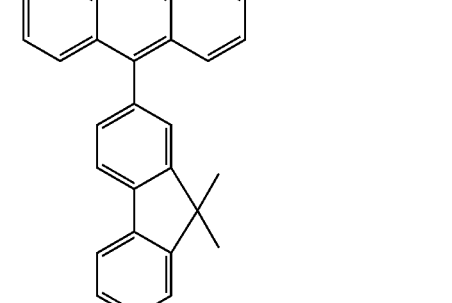
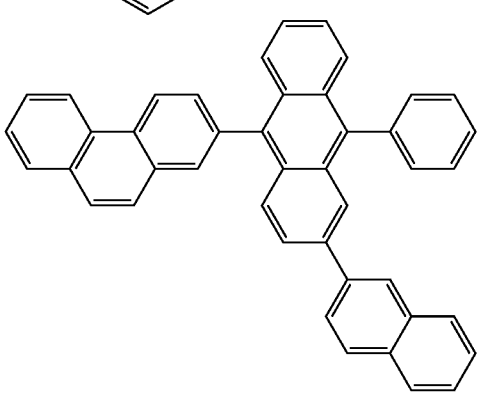
In some embodiments, an anthracene-based compound represented by Formula 401 below may be used as the host.

<Formula 401>

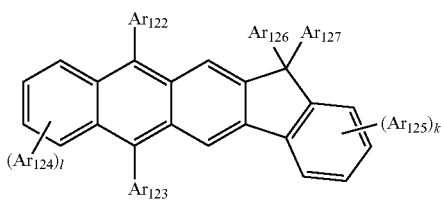

Ar$_{122}$ to Ar$_{125}$ in Formula 401 above may be defined as described above in conjunction with Ar$_{113}$ of Formula 400, and thus detailed descriptions thereof will not be provided here.

Ar$_{126}$ and Ar$_{127}$ in Formula 401 above may be each independently a $C_1$-$C_{10}$ alkyl group, for example, one of a methyl group, an ethyl group and a propyl group.

In Formula 401, k and l may be each independently an integer from 0 to 4, for example, 0, 1, or 2.

For example, the anthracene compound of Formula 401 above may be one of the compounds represented by the following formulae, but it is not limited thereto:

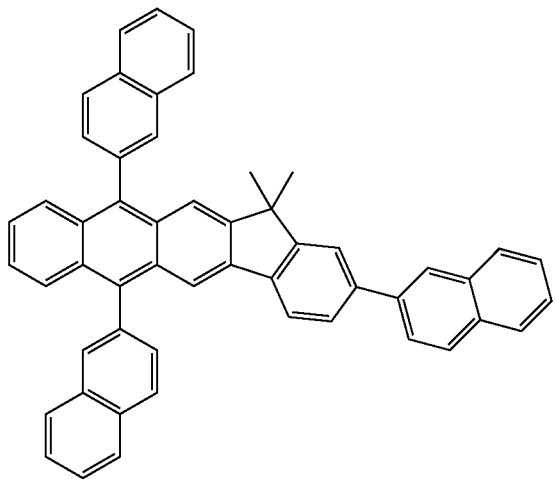

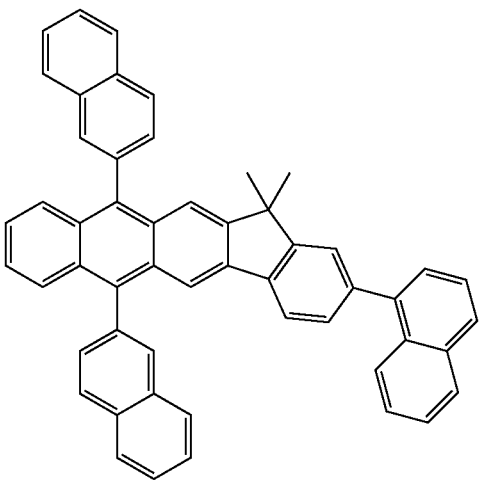

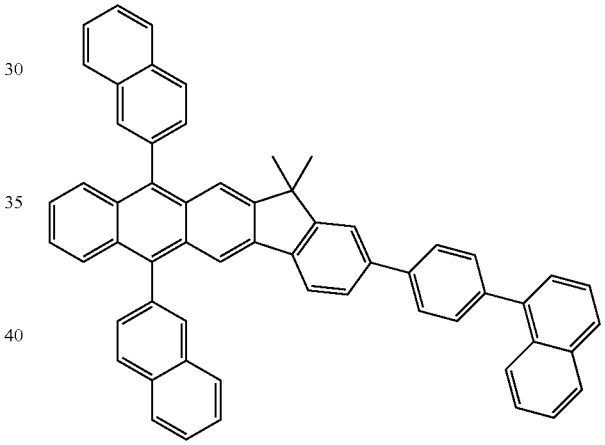

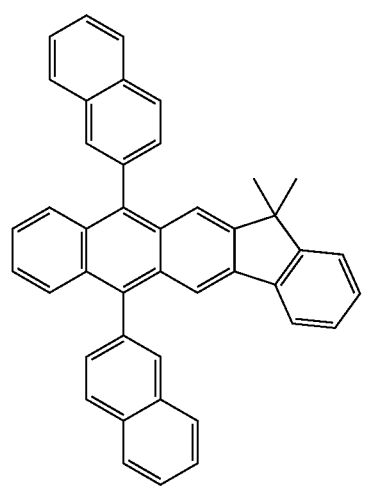

The dopant may be any effective dopant, for example, at least one of a fluorescent dopant and a phosphorescent dopant may be used. For example, the phosphorescent dopant may be, but is not limited to, an organometallic complex including at least one selected from iridium (Ir), platinum (Pt), osmium (Os), rhenium (Re), titanium (Ti), zirconium (Zr), hafnium (Hf), europium (Eu), terbium (Tb), and thulium (Tm).

Non-limiting examples of widely known blue dopants are the following compounds, including F$_2$Irpic (bis[3,5-difluoro-2-(2-pyridyl)phenyl](picolinato)iridium(III)), (F$_2$ppy)$_2$Ir(tmd), Ir(dfppz)$_3$, DPVBi (4,4'-bis(2,2'-diphenylethen-1-yl)biphenyl), DPAVBi (4,4'-bis[4-(diphenylamino)styryl]biphenyl), and TBPe (2,5,8,11-tetra-tert-butyl perylene).

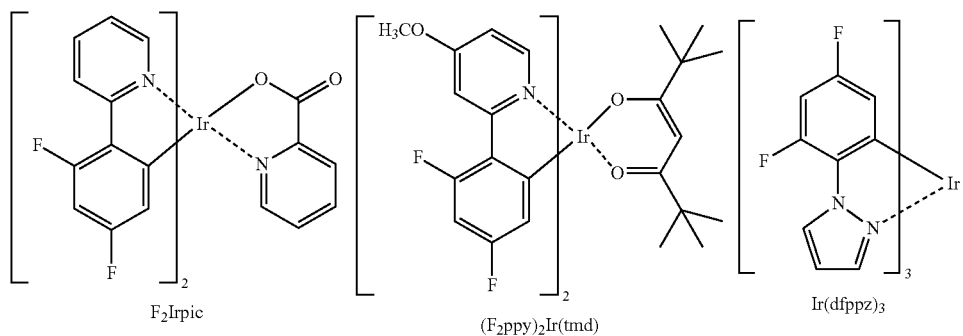
F₂Irpic      (F₂ppy)₂Ir(tmd)      Ir(dfppz)₃
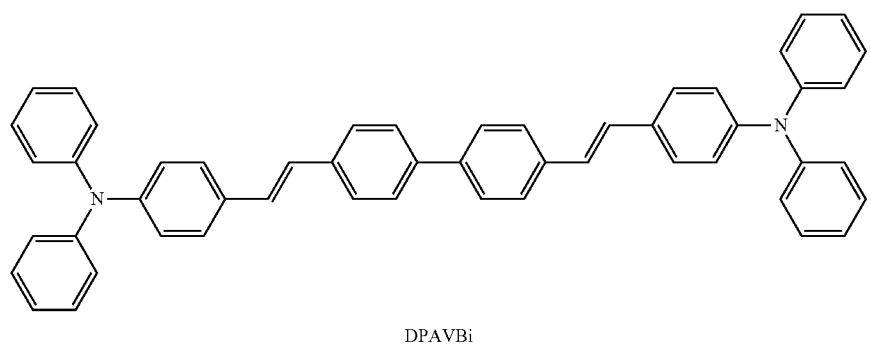
DPAVBi
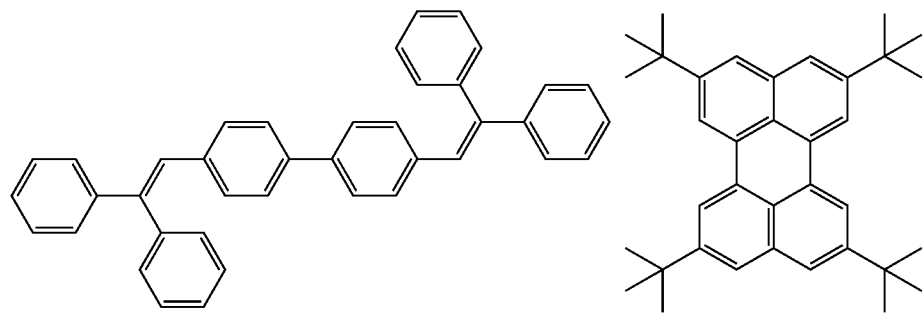
DPABi      TPBe
Non-limiting examples of effective blue dopants are compounds represented by the following formulae, but they are not limited thereto.
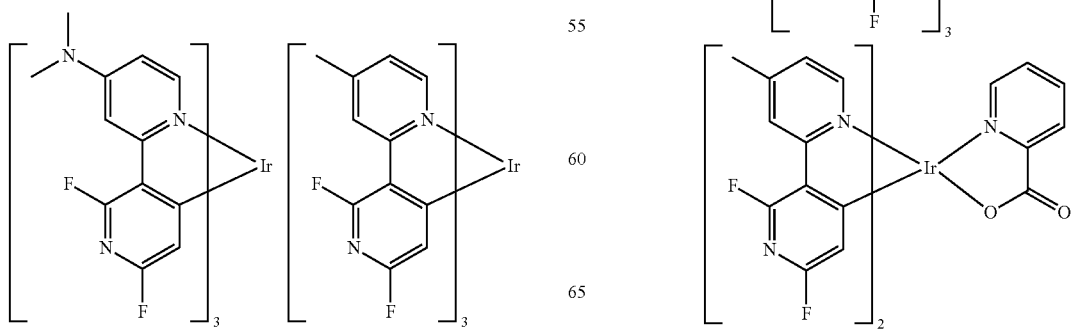

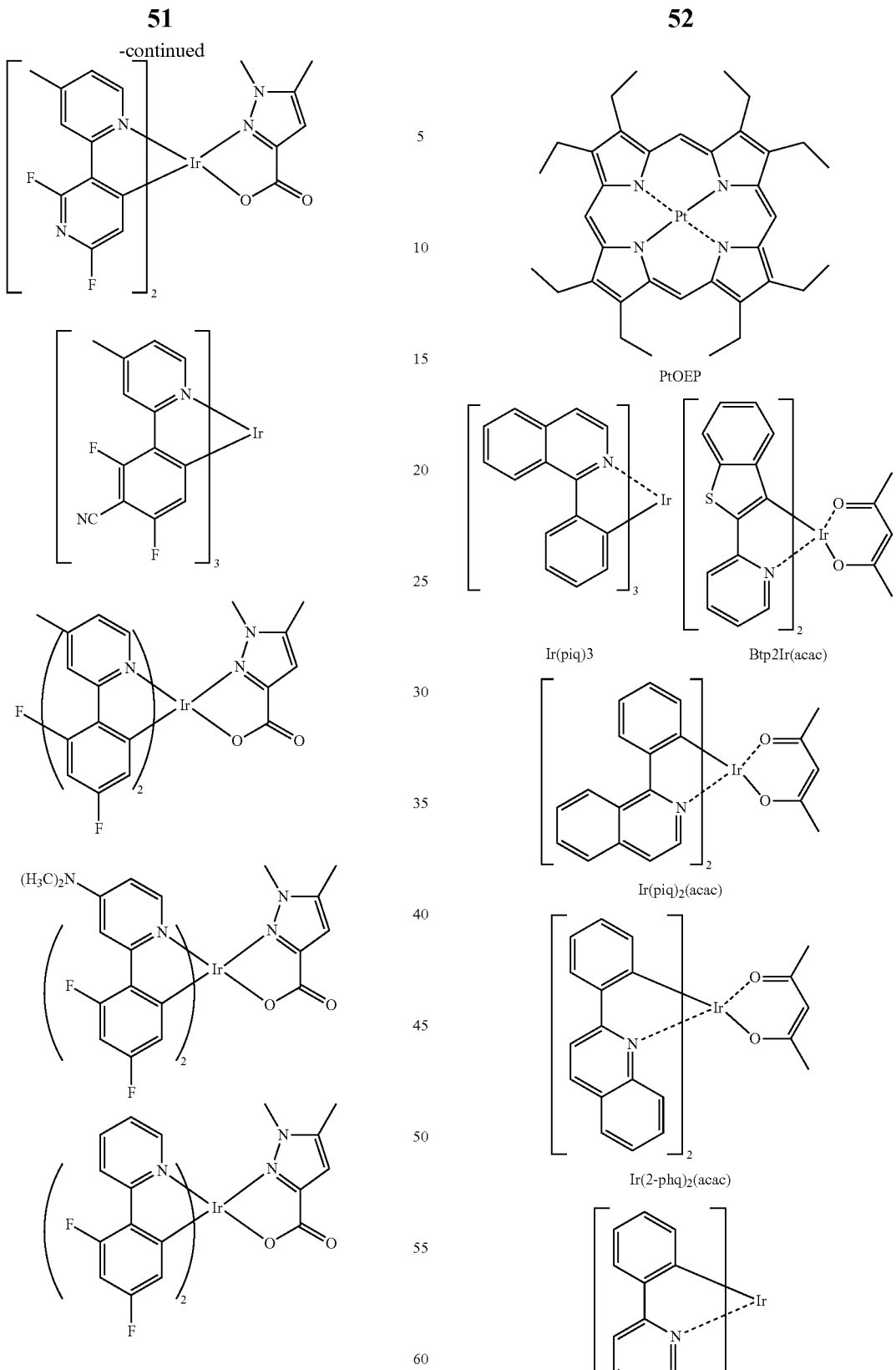
Non-limiting examples of effective red dopants are PtOEP (Pt(II) octaethylporphine), Ir(piq)$_3$ (tris(2-phenylisoquinoline)iridium), Btp$_2$Ir(acac) (bis(2-(2'-benzothienyl)-pyridinato-N,C3')iridium(acetylacetonate)), DCM (4-(dicyanomethylene)-2-methyl-6-[p-(dimethylamino)styryl]-4H-pyran), DCJTB (4-(dicyanomethylene)-2-tert-butyl-6-(1,1,7,7,-tetramethyljulolidyl-9-enyl)-4H-pyran).

-continued

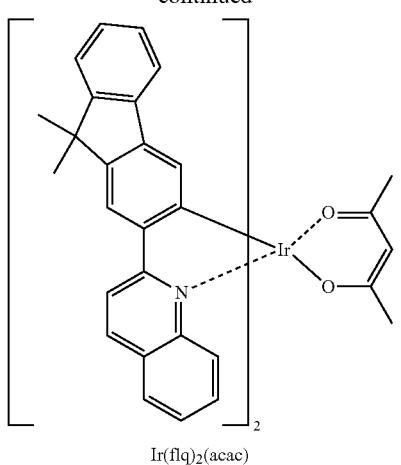

Ir(flq)₂(acac)

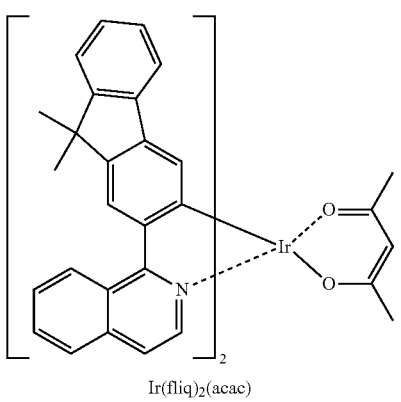

Ir(fliq)₂(acac)

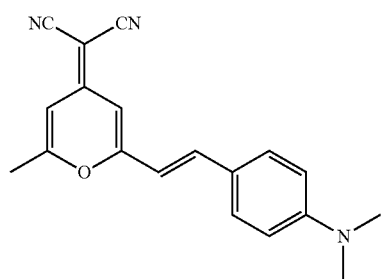

DCM

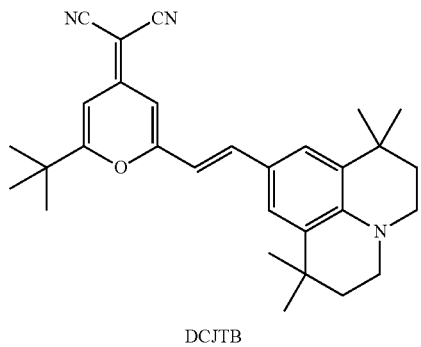 [SMILES: CC(C)(C)C1=CC(=C(C#N)C#N)C=C(/C=C/c2cc3c4c(c2)C(C)(C)CCN4CCC3(C)C)O1]

DCJTB

Non-limiting examples of effective green dopants are Ir(ppy)₃ (tris(2-phenylpyridine) iridium), Ir(ppy)₂(acac) (bis(2-phenylpyridine)(acetylacetonato)iridium(III), Ir(mppy)₃ (tris(2-(4-tolyl)phenylpiridine)iridium), and C545T (10-(2-benzothiazolyl)-1,1,7,7-tetramethyl-2,3,6,7-tetrahydro-1H,5H,11H-[1]benzopyrano[6,7,8-ij]-quinolizin-11-one).

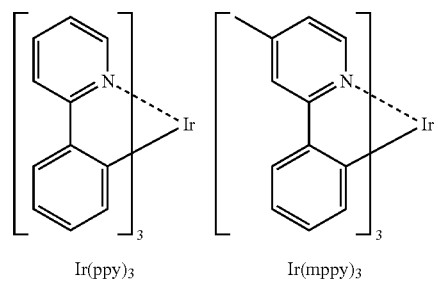

Ir(ppy)₃        Ir(mppy)₃

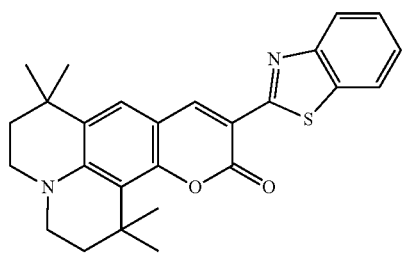

Ir(ppy)₂(acac)

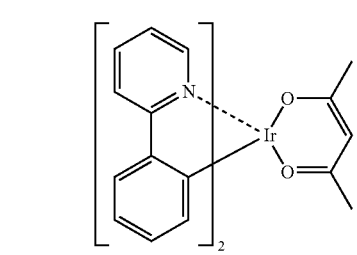

C545T

Non-limiting examples of the dopant that may be used in the EML are Pt complexes represented by Formulae D1-D50:

D1

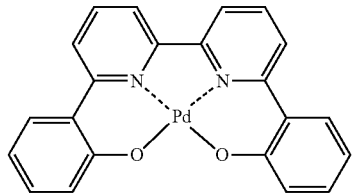

D2

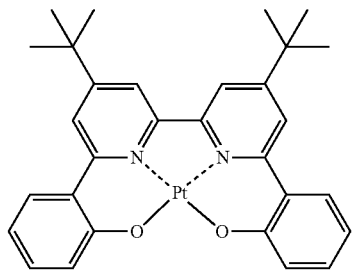

D3 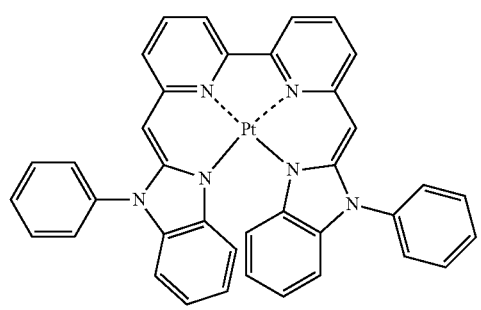
D4 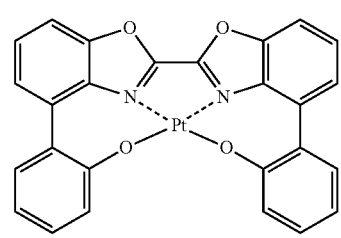
D5 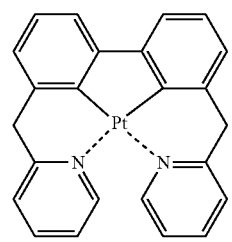
D6 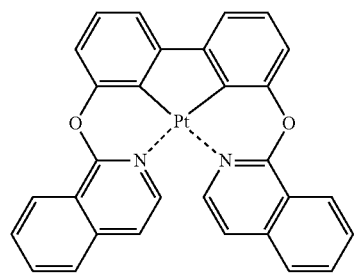
D7 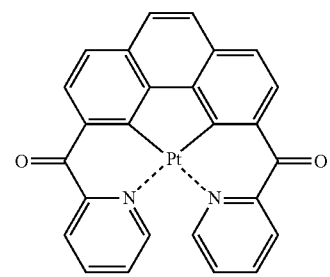
D8 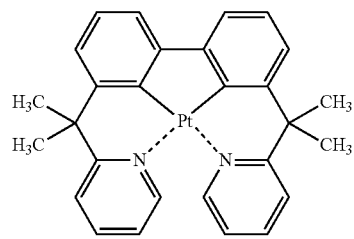
D9 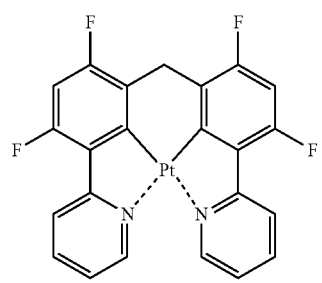
D10 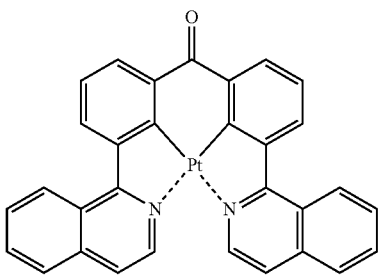
D11 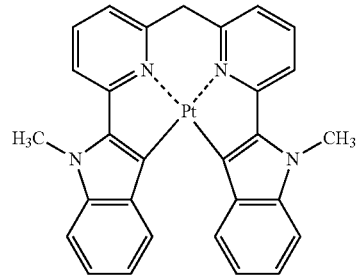
D12 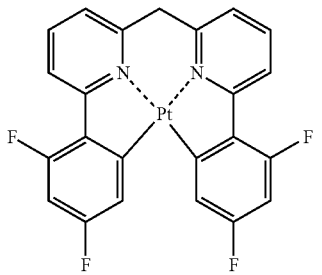
D13 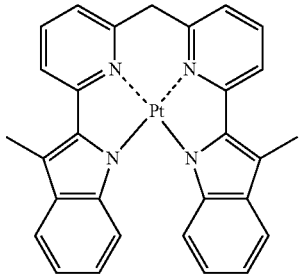

-continued
D14
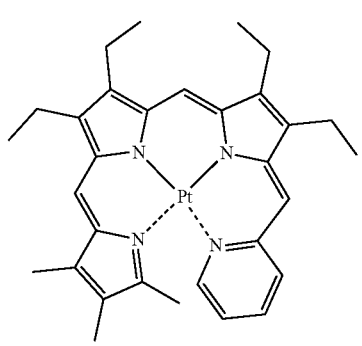
D15
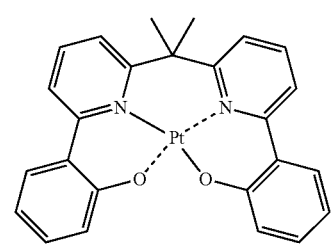
D16
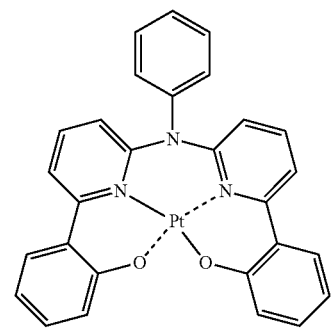
D17
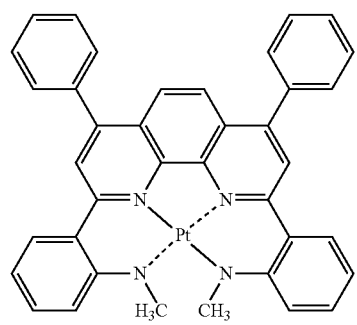
D18
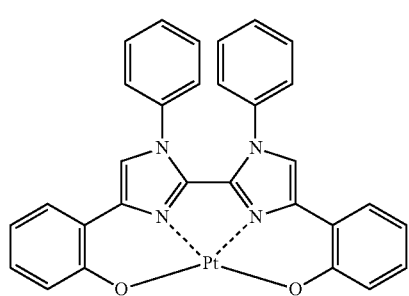
-continued
D19
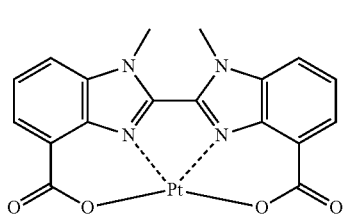
D20
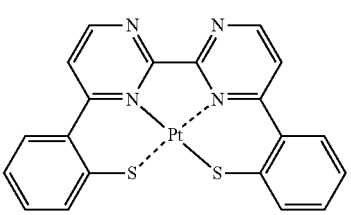
D21
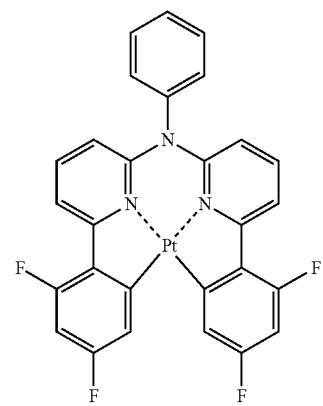
D22
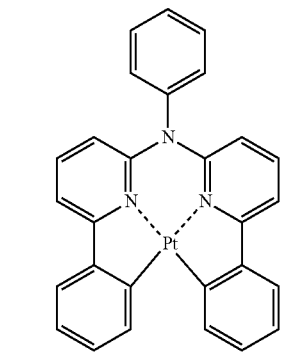
D23
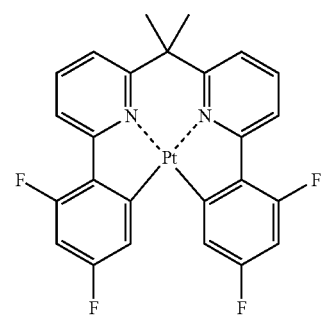

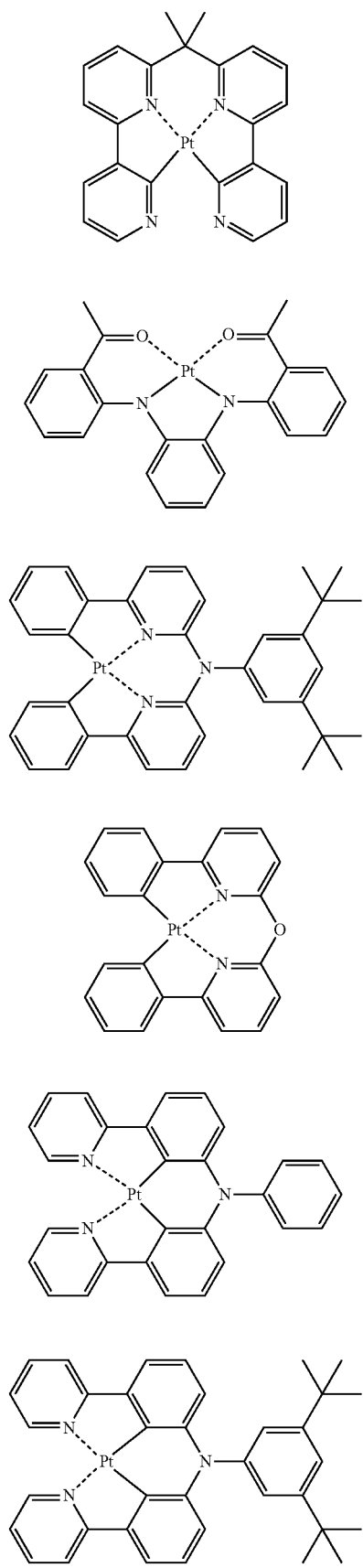
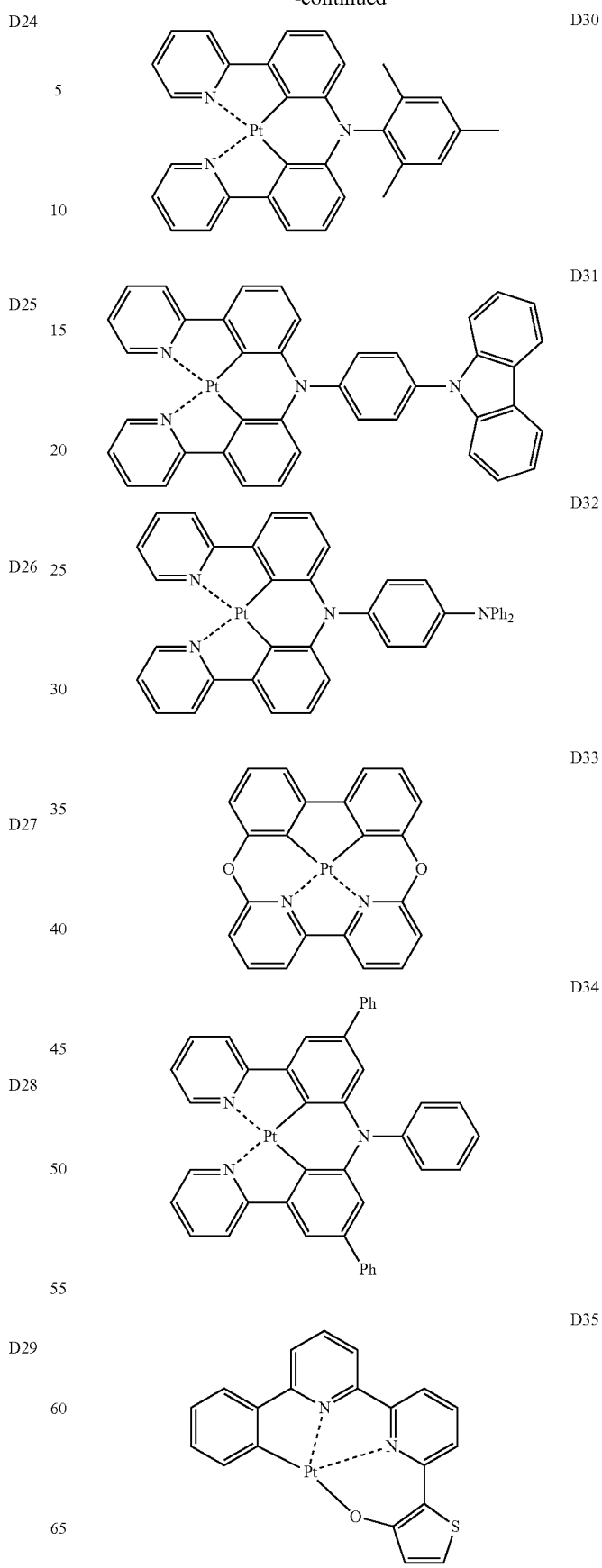

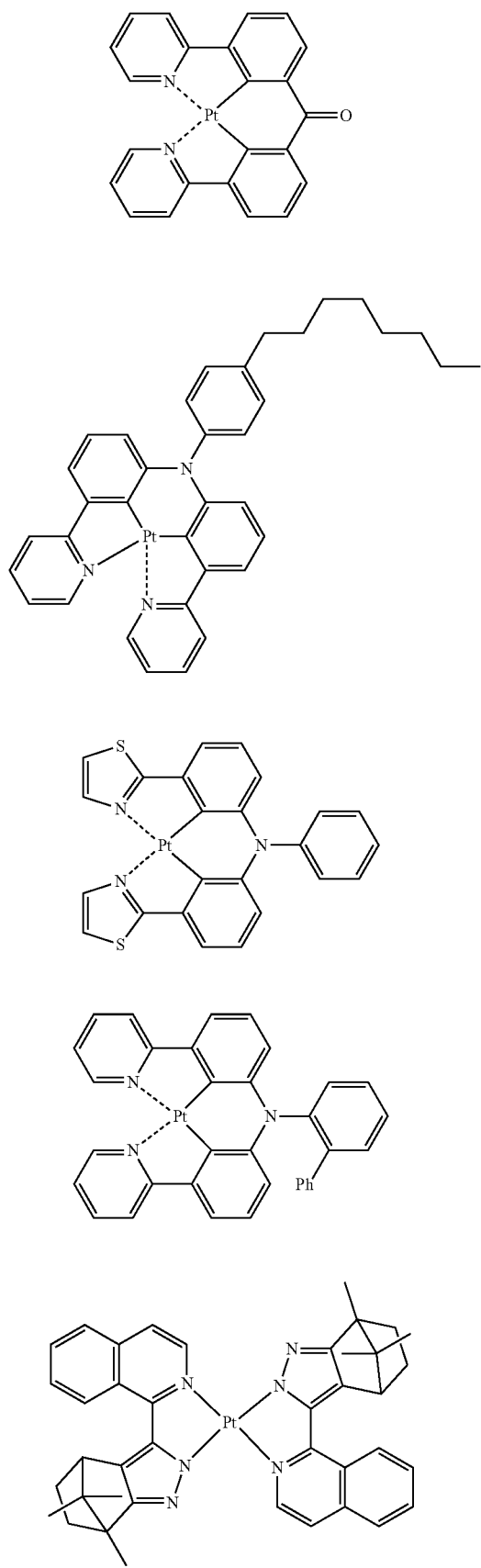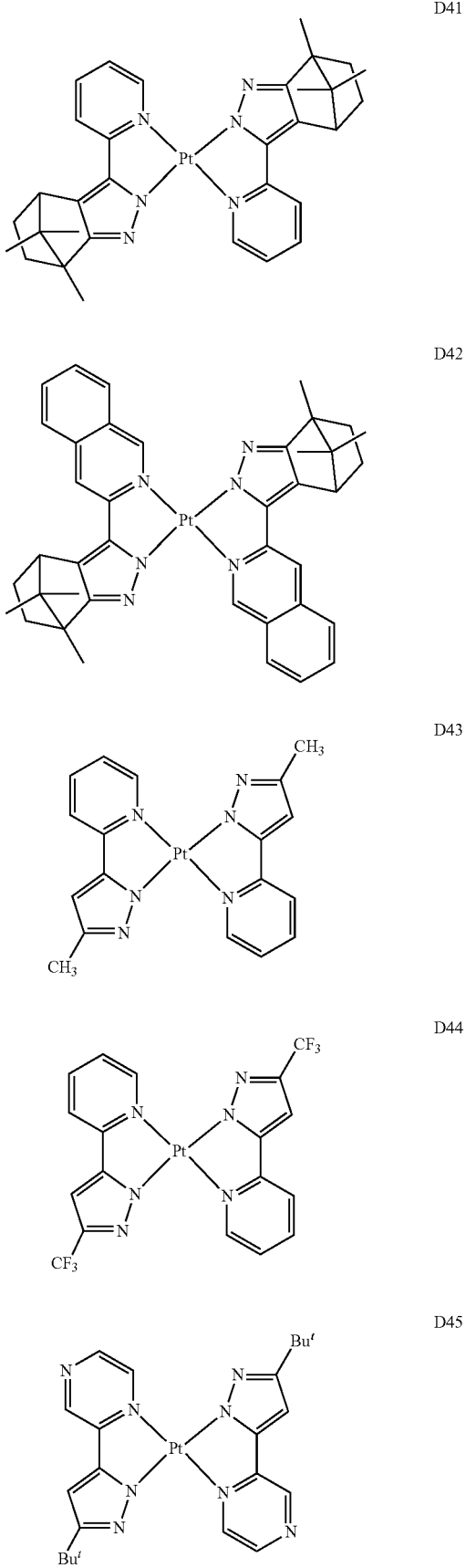

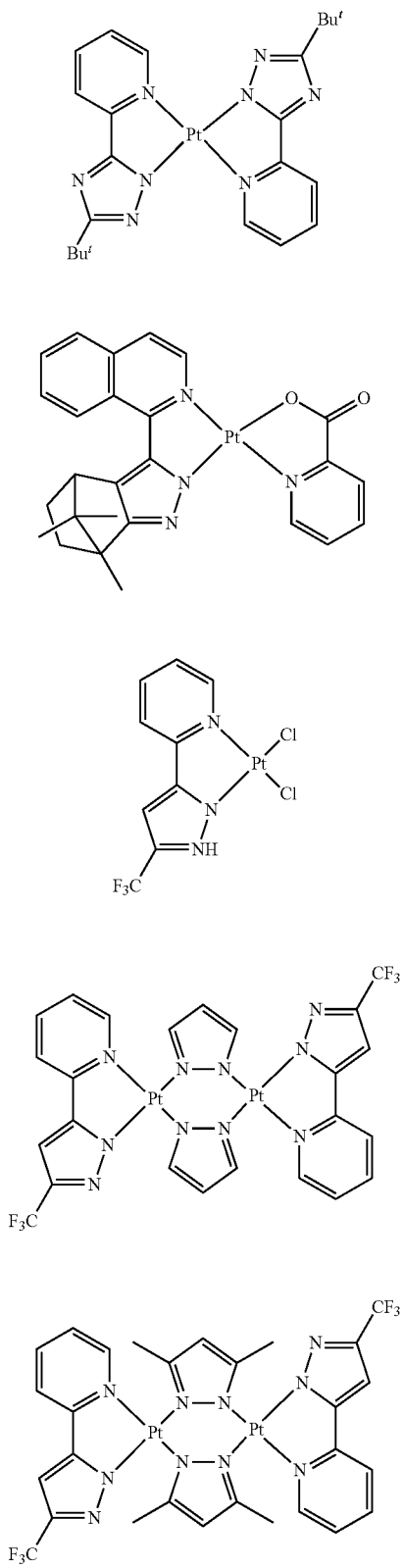
D46
D47
D48
D49
D50
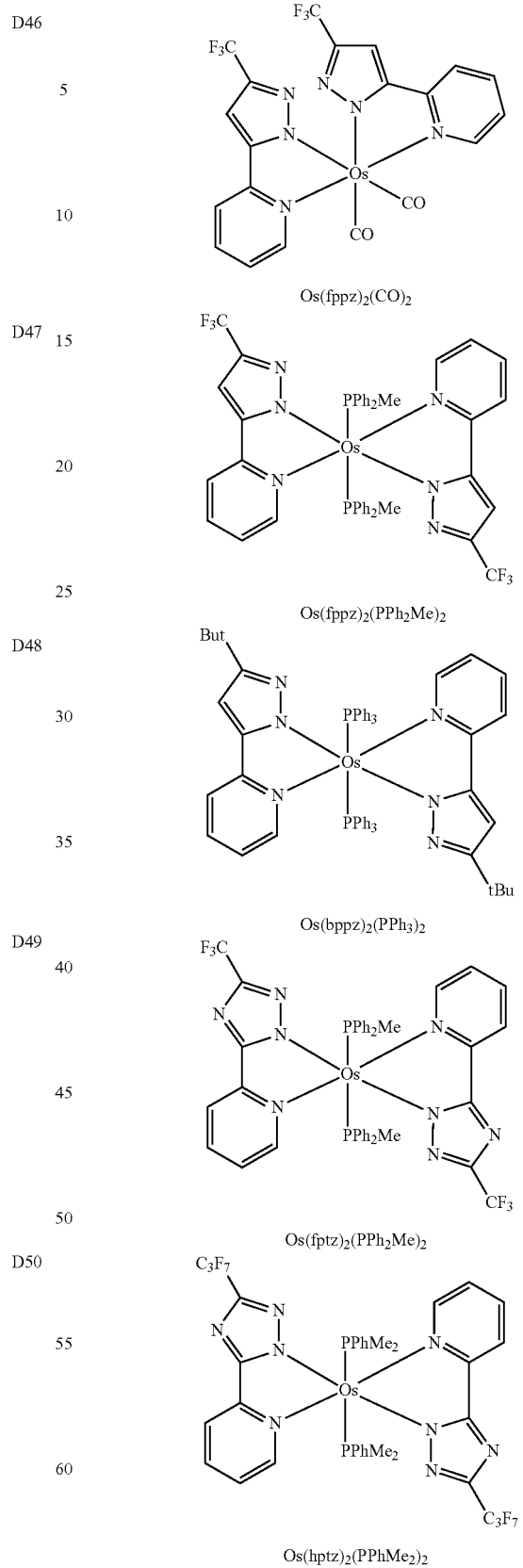
Os(fppz)₂(CO)₂
Os(fppz)₂(PPh₂Me)₂
Os(bppz)₂(PPh₃)₂
Os(fptz)₂(PPh₂Me)₂
Os(hptz)₂(PPhMe₂)₂
Non-limiting examples of the dopant that may be used in the EML are Os complexes represented by the following formulae:
When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1000 Å, and, in some embodiments, may be from about 200 Å to about 600 Å. When the thickness of the EML is within these ranges, the EML may have good light emitting ability without imparting a substantial increase in driving voltage to an OLED including it.

To prevent diffusion of triplet excitons or holes into the ETL, a hole blocking layer (HBL) may be formed between the HTL and the EML by using one of vacuum deposition, spin coating, casting, Langmuir-Blodgett (LB) deposition, and the like. When the HBL is formed using one of vacuum deposition and spin coating, the conditions for deposition and coating may be similar to those for the formation of the HIL, although the conditions for deposition and coating may vary according to the material that is used to form the HBL. Any effective hole-blocking material may be used. Non-limiting examples of hole-blocking materials are oxadiazole derivatives, triazole derivatives, and phenanthroline derivatives. For example, 2,9-dimethyl-4,7-diphenyl-1,10-phenanthroline (BCP) may be used as a material for forming the HBL.

The thickness of the HBL may be from about 50 Å to about 1000 Å, and in some embodiments, from about 100 Å to about 300 Å. When the thickness of the HBL is within these ranges, the HBL may have improved hole blocking ability without imparting a substantial increase in driving voltage to an OLED including it.

Then, an ETL may be formed on the HBL or EML by one of vacuum deposition, spin coating, casting, and the like. When the ETL is formed using one of vacuum deposition and spin coating, the deposition and coating conditions may be similar to those for the formation of the HIL, though the deposition and coating conditions may vary according to the material that is used to form the ETL. As a material for forming the ETL, the condensed cyclic compound of Formula 1 or any material that may stably transport electrons injected from an electron injecting electrode (cathode) may be used.

Non-limiting examples of widely known ETL materials are quinoline derivatives, such as Alq$_3$ (tris(8-quinolinole) aluminum), BCP (2,9-dimethyl-4,7-diphenyl-1,10-phenanthroline), Bphen (4,7-diphenyl-1,10-phenanthroline; 4,7-diphenyl-1,10-phenanthroline), TAZ (3-(4-biphenylyl)-4-phenyl-5-tert-butylphenyl-1,2,4-triazole), NTAZ (4-(Naphthalen-1-yl)-3,5-diphenyl-4H-1,2,4-triazole), tBu-PBD (2-(4-biphenylyl)-5-(4-tert-butylphenyl)-1,3,4-oxadiazole, BAlq (see the following formula), Bebq$_2$ (beryllium bis(benzoquinolin-10-olate), ADN (9,10-di(naphthalene-2-yl) anthracene), Compound 501, and Compound 502.

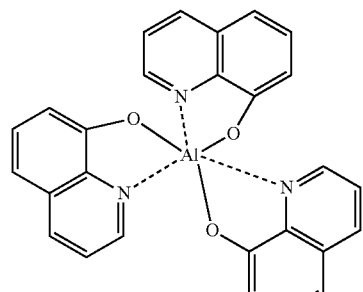

Alq3

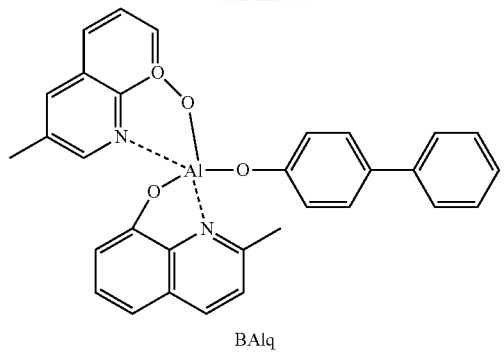

BAlq

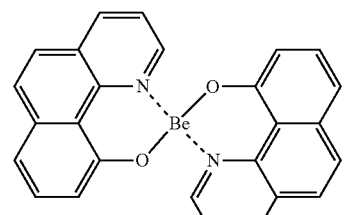

Bebq2

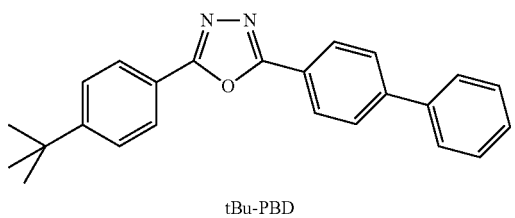

tBu-PBD

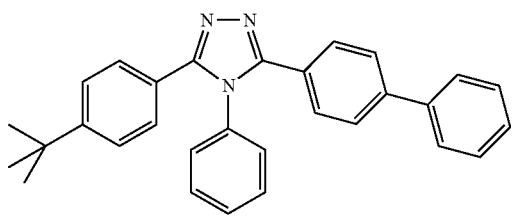

TAZ

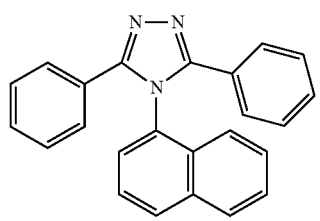

NTAZ

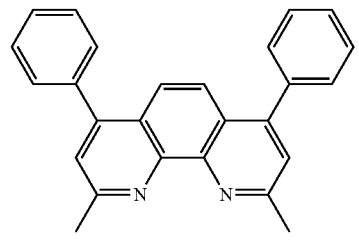

BCP

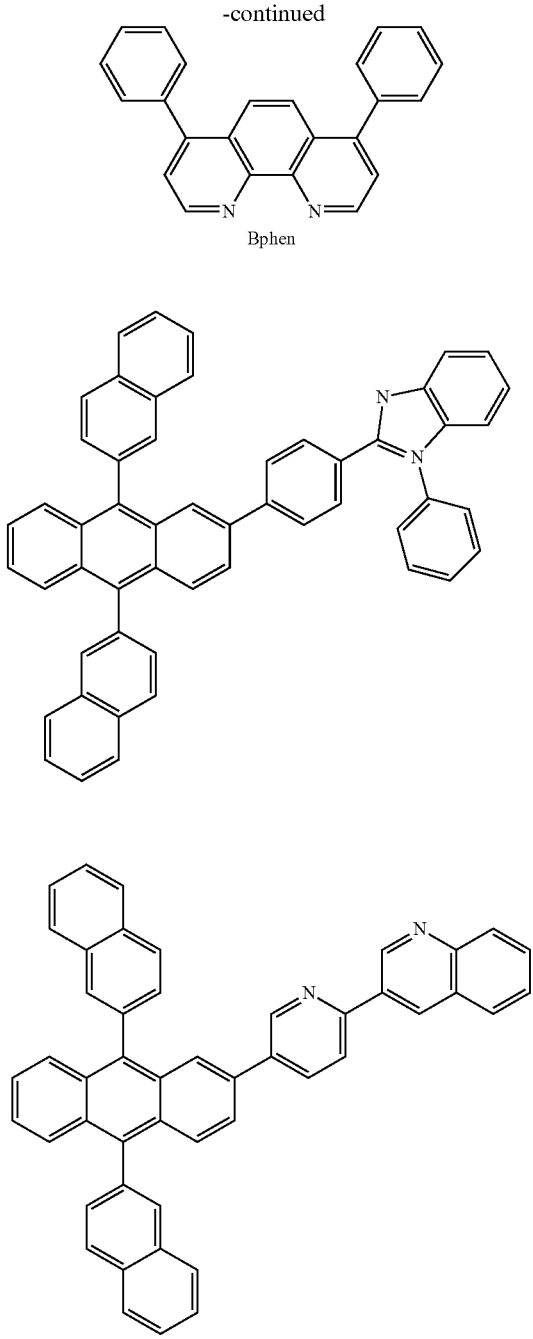

The thickness of the ETL may be from about 100 Å to about 1,000 Å, and, in some embodiments, may be from about 150 Å to about 500 Å. When the thickness of the ETL is within these ranges, the ETL may have satisfactory electron transporting ability without imparting a substantial increase in driving voltage to an OLED including it.

In some embodiments, the ETL may include an electron-transporting organic compound as described above and a metal-containing material. The metal-containing material may include a lithium (Li) complex. Non-limiting examples of the Li complex are lithium quinolate (LiQ) and Compound 503 below:

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and, in some embodiments, may be from about 3 Å to about 90 Å. When the thickness of the EIL is within these ranges, the EIL may have satisfactory electron injection ability without imparting a substantial increase in driving voltage to an OLED including it.

The second electrode 17 is disposed on the organic layer 15. The second electrode 17 may be a cathode that is an electron injection electrode. A material for forming the second electrode 17 may be one of a metal, an alloy, an electro-conductive compound that has a low work function, and a mixture thereof. In this regard, the second electrode 17 may be formed of one of lithium (Li), magnesium (Mg), aluminum (Al), aluminum (Al)-lithium (Li), calcium (Ca), magnesium (Mg)-indium (In), magnesium (Mg)-silver (Ag), and the like, and may be formed as a thin film type transmission electrode. In some embodiments, to manufacture a top-emission light-emitting device, the transmission electrode may be formed of one of indium tin oxide (ITO) and indium zinc oxide (IZO).

Hereinafter, the present invention will be described in detail with reference to the following synthesis examples and other examples. However, these examples are for illustrative purposes only and are not intended to limit the scope of the present invention.

SYNTHESIS EXAMPLE

Synthesis Example 1

Synthesis of Compound 1

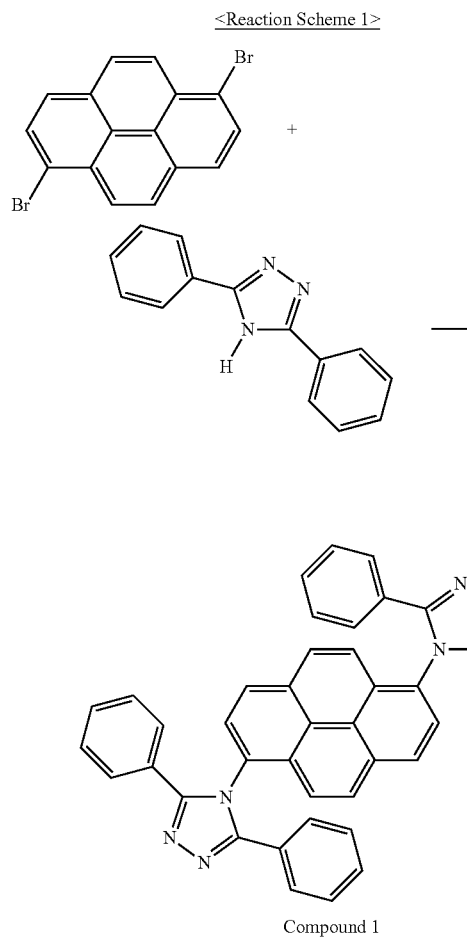

Compound 1

Quantities of 3.6 g (10 mmol) of 1,6-dibromopyrene, 6.6 g (30 mmol) of 3,5-diphenyl-4H-1,2,4-triazole, 180 mg (0.8 mol) of palladium acetate (Pd(OAc)$_2$), 660 mg (4.0 mmol) of tri-tert-butylphosphine (P(t-Bu)$_3$), and 5.4 g (60 mmol) of sodium t-butoxide were added to 100 ml of toluene, and then refluxed in a nitrogen atmosphere for about 12 hours. After completion of the reaction, the solvent was removed by evaporation. The resultant residue was washed with 500 ml of methylene chloride and 500 ml of water. Then, an organic layer was collected and dried using anhydrous magnesium sulfate, followed by recrystallization and silica gel chromatography to obtain 3.7 g of Compound 1 (Yield: 58%).

H-NMR (CDCl$_3$, 300 MHz, ppm): 8.3-8.2 (m, 8H), 8.0-7.8 (m, 4H), 7.7-7.6 (m, 4H), 7.5-7.4 (m, 12H)

MS (MALDI-TOF) m/z: 640 [M]+.

Synthesis Example 2

Synthesis of Compound 9

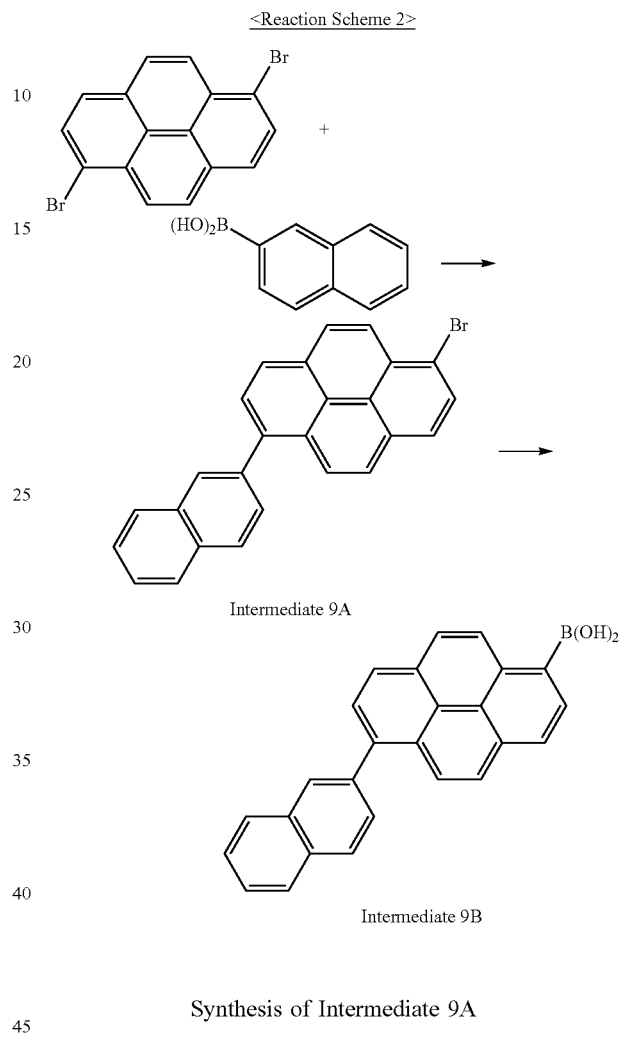

Intermediate 9A

Intermediate 9B

Synthesis of Intermediate 9A

Quantities of 3.6 g (10 mmol) of 1,6-dibromopyrene, 2.1 g (12 mmol) of 2-naphthyl boronic acid, 0.46 g (0.4 mmol) of Pd(PPh$_3$)$_4$, 6 mL of a 2M K$_2$CO$_3$ aqueous solution, 25 mL of toluene, and 13 mL of ethanol were combined and refluxed in a nitrogen atmosphere for about 12 hours while stirring. The resulting product was washed with distilled water, and an organic component was extracted with ethyl acetate (EA). The extracted organic component was dried using anhydrous MgSO$_4$, and then distilled under reduced pressure. The resulting product was subjected to column separation to obtain 3.6 g (88%) of Intermediate 9A.

Synthesis of Intermediate 9B

A quantity of 3.6 g (8.8 mmol) of Intermediate 9A was dissolved in a flask containing 100 ml of tetrahydrofuran at room temperature. After the temperature of the flask was cooled down to about −78° C., 6.2 mL (10.0 mol) of n-butyl lithium was slowly dropwise added to the solution, and then 2.6 mL (11.0 mol) of triisopropyl borate was then slowly dropwise added thereto, while the temperature was maintained. Afterward, the temperature of the flask was slowly increased to room temperature overnight for reaction. After completion of the reaction, a 1N-HCl aqueous solution was added to the reaction solution until the pH reached 2 to acidify the reaction solution. An organic layer was extracted from the acidified reaction solution using ethyl acetate, and the ethyl acetate extracts were then washed with purified water. After separating the ethyl acetate from the organic layer, the organic layer was dried using anhydrous magnesium sulfate and filtered. The filtrate was concentrated and then recrystallized with dichloromethane and n-hexane to obtain 2.4 g (Yield 74%) of Intermediate 9B.

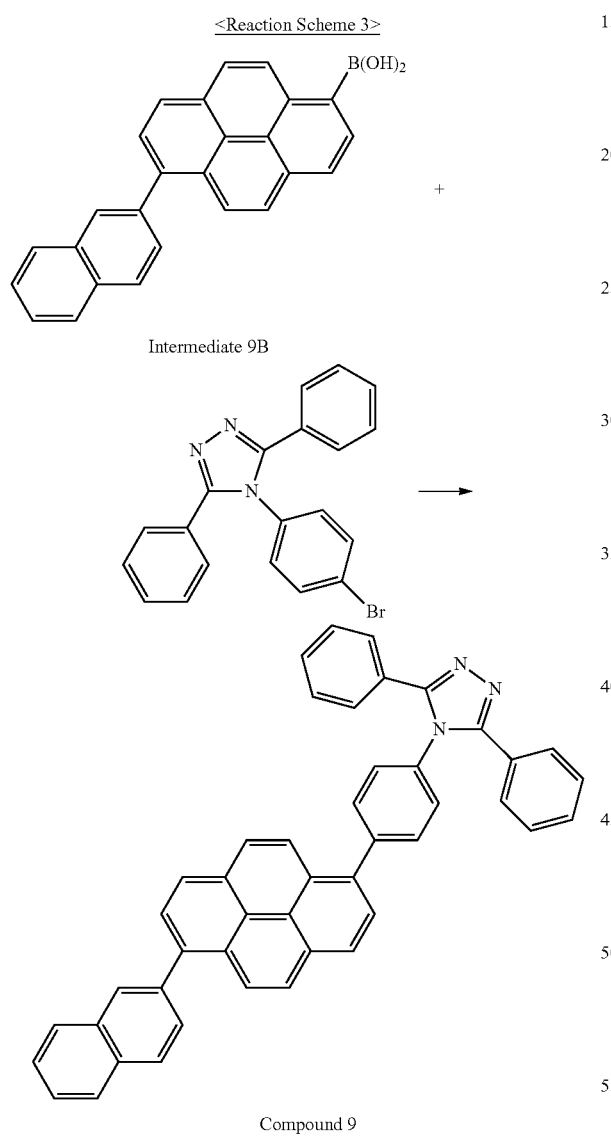

Compound 9

A quantity of 3.2 g of Compound 9 (Yield 81%) was synthesized in the same manner as the method of synthesizing Intermediate 9A, except that Intermediate 9B and 4-(4-bromophenyl)-3,5-diphenyl-4H-1,2,4-triazole, instead of 2-naphthyl boronic acid and 1,6-dibromopyrene, were used.

H-NMR (CDCl$_3$, 300 MHz, ppm): 8.3-8.2 (m, 5H), 8.0-7.9 (m, 6H), 7.8-7.7 (m, 9H), 7.6-7.4 (m, 9H).

MS (MALDI-TOF) m/z: 623 [M]+.

Synthesis Example 3

Synthesis of Compound 11

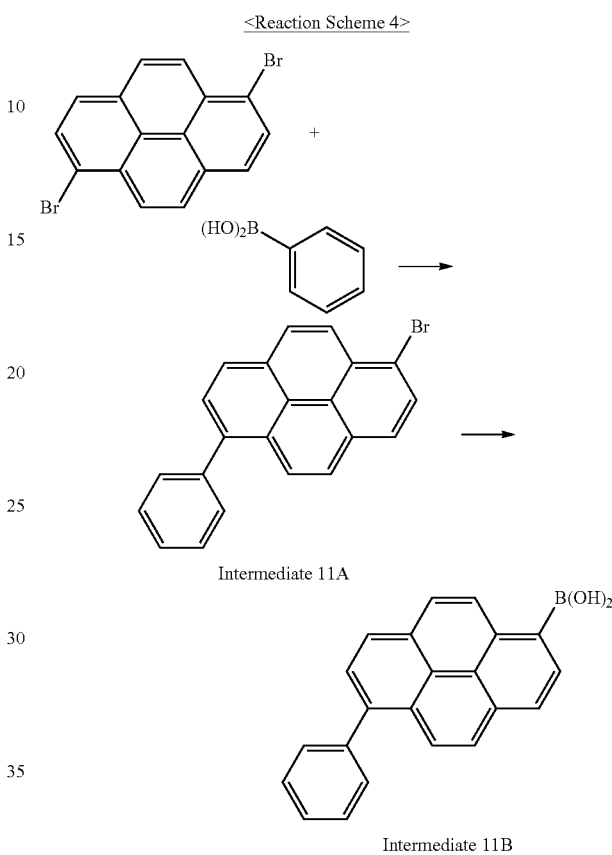

Synthesis of Intermediate 11A

A quantity of 2.8 g of Intermediate 11A (Yield 78%) was synthesized in the same manner as the method of synthesizing Intermediate 9A, except that phenyl boronic acid, instead of 2-naphthyl boronic acid, was used.

Synthesis of Intermediate 11B

A quantity of 1.7 g of Intermediate 11B (Yield 70%) was synthesized in the same manner as the method of synthesizing Intermediate 9B, except that Intermediate 11A, instead of Intermediate 9A, was used.

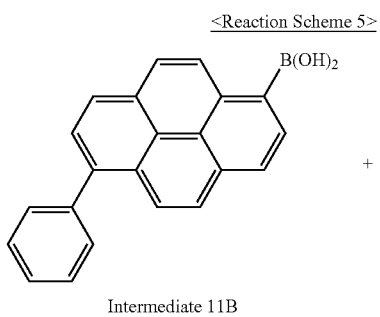

Intermediate 11B

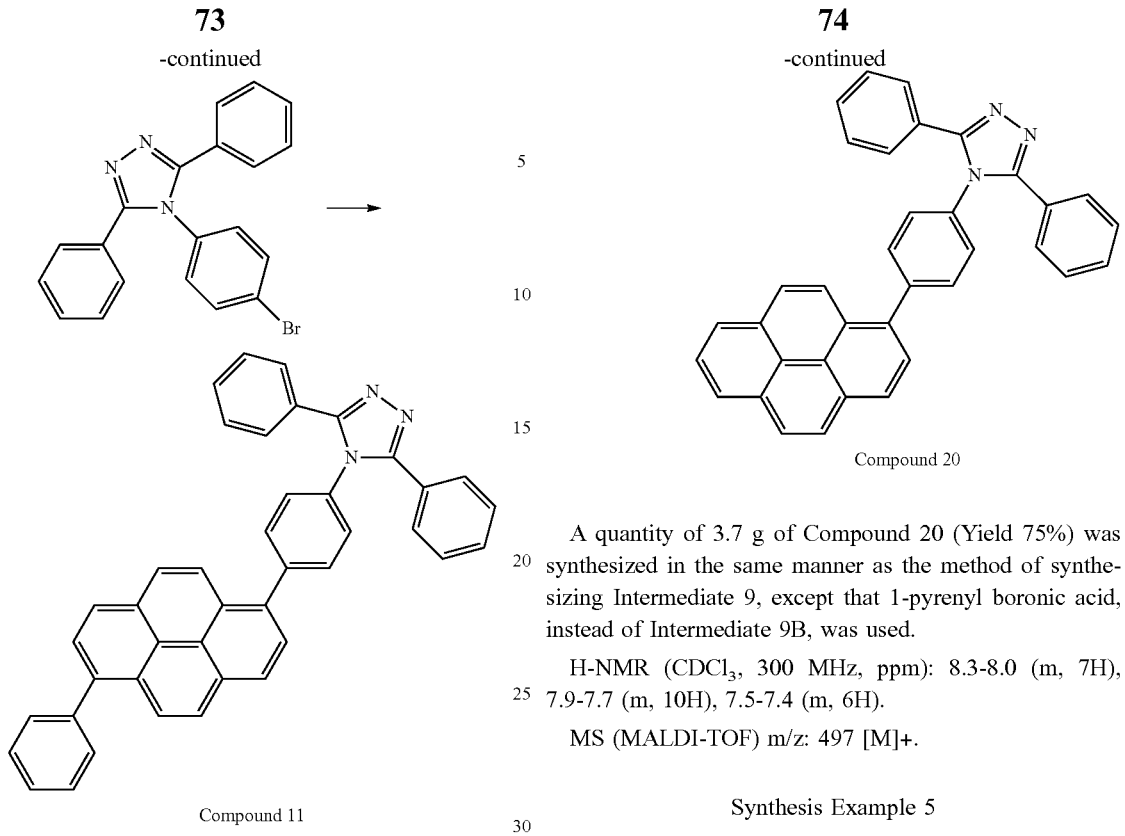

Compound 11

A quantity of 2.6 g of Compound 11 (Yield 83%) was synthesized in the same manner as the method of synthesizing Compound 9, except that Intermediate 11B, instead of Intermediate 9B, was used.

H-NMR (CDCl$_3$, 300 MHz, ppm): 8.3-8.2 (m, 5H), 8.1-8.0 (m, 3H), 7.8-7.7 (m, 10H), 7.5-7.4 (m, 9H).

MS (MALDI-TOF) m/z: 573 [M]+.

Synthesis Example 4

Synthesis of Compound 20

<Reaction Scheme 6>

Compound 20

A quantity of 3.7 g of Compound 20 (Yield 75%) was synthesized in the same manner as the method of synthesizing Intermediate 9, except that 1-pyrenyl boronic acid, instead of Intermediate 9B, was used.

H-NMR (CDCl$_3$, 300 MHz, ppm): 8.3-8.0 (m, 7H), 7.9-7.7 (m, 10H), 7.5-7.4 (m, 6H).

MS (MALDI-TOF) m/z: 497 [M]+.

Synthesis Example 5

Synthesis of Compound 21

<Reaction Scheme 7>

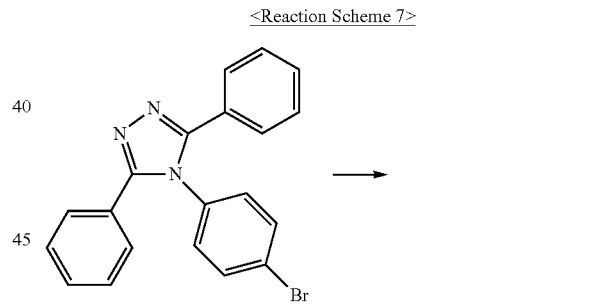

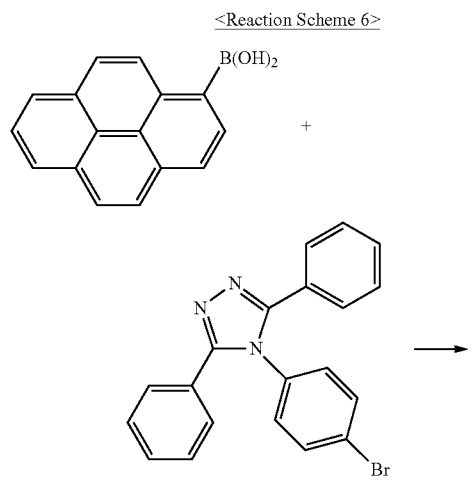

Intermediate 21A

A quantity of 9.3 g of Intermediate 21A (Yield 68%) was synthesized in the same manner as the method of synthesizing Intermediate 9B, except that 4-(4-bromophenyl)-3,5-diphenyl-4H-1,2,4-triazole, instead of Intermediate 9A, was used.

<Reaction Scheme 8>

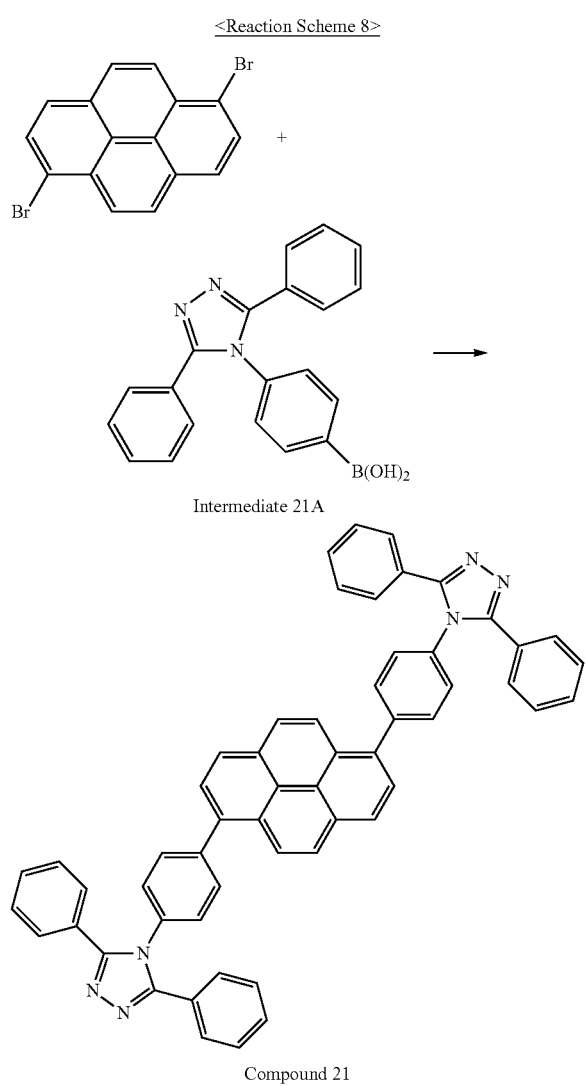

Compound 21

A quantity of 4.3 g of Compound 21 (Yield 54%) was synthesized in the same manner as the method of synthesizing Intermediate 9, except that Intermediate 21A and 1,6-dibromopyrene, instead of Intermediate 9B and 4-(4-bromophenyl)-3,5-diphenyl-4H-1,2,4-triazole, were used.

H-NMR (CDCl$_3$, 300 MHz, ppm): 8.3-8.2 (m, 8H), 8.1-8.0 (m, 4H), 7.9-7.7 (m, 12H), 7.5-7.4 (m, 12H).

MS (MALDI-TOF) m/z: 792 [M]+.

Example 1

A 15 Ω/cm² (1200 Å) ITO glass substrate (available from Corning Co.) was cut to a size of 50 mm×50 mm×0.5 mm, ultrasonically washed with isopropyl alcohol for 5 minutes and then with pure water for 5 minutes, and washed again with UV-generated ozone for 30 minutes. m-MTDATA was vacuum-deposited on the ITO glass substrate to form a HIL having a thickness of 600 Å on the anode, and then α-NPD was vacuum-deposited on the HIL to form a HTL having a thickness of 300 Å. (E)-4-(2-([1,1':4',1''-terphenyl-4-yl)vinyl)-N,N-diphenylaniline (BD1) and 2-methyl-9,10-di(naphthalene-2-yl)anthracene (MADN) as represented by the following formulae were vacuum-deposed as a dopant and a host, respectively, on the HTL at a deposition rate of about 0.05 Å/sec and about 1 Å/sec, respectively, to form a blue EML having a thickness of about 200 Å.

Compound 1 was vacuum-deposited on the EML to form an ETL having a thickness of 300 Å. LiF was vacuum-deposited on the ETL to form an EIL having a thickness of 10 Å and Al was vacuum-deposited on the EIL to form a cathode having a thickness of 3,000 Å, thereby completing the manufacture of an organic light-emitting device.

Example 2

An organic light-emitting device was manufactured in the same manner as in Example 1, except that Compound 9, instead of Compound 1, was used as an ETL material.

Example 3

An organic light-emitting device was manufactured in the same manner as in Example 1, except that Compound 11, instead of Compound 1, was used as an ETL material.

Example 4

An organic light-emitting device was manufactured in the same manner as in Example 1, except that Compound 20, instead of Compound 1, was used as an ETL material.

Example 5

An organic light-emitting device was manufactured in the same manner as in Example 1, except that Compound 21, instead of Compound 1, was used as an ETL material.

Comparative Example 1

An organic light-emitting device was manufactured in the same manner as in Example 1, except that Alq$_3$, instead of Compound 1, was used as an ETL material.

Comparative Example 2

An organic light-emitting device was manufactured in the same manner as in Example 1, except that Compound C-1 below, instead of Compound 1, was used as an ETL material.

<C-1>

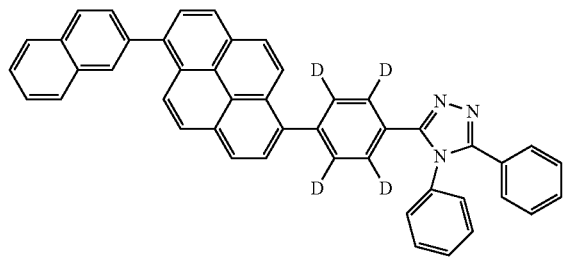

Comparative Example 3

An organic light-emitting device was manufactured in the same manner as in Example 1, except that NTAZ, instead of Compound 1, was used as an ETL material.

NTAZ

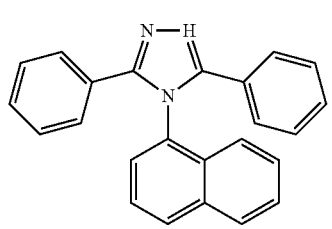

Evaluation Example

Driving voltages, current densities, luminance, efficiencies, emitting-light colors, half-life spans of the organic light-emitting devices of Examples 1 to 5 and Comparative Examples 1 to 3 were measured using a PR650 (Spectroscan) Source Measurement Unit. (available from Photo Research, Inc.). The results are shown in Table 1 below.

TABLE 1

| | EML | ETL | Luminance (cd/m$^2$) | Current density (mA/cm$^2$) | Driving voltage (V) | Color coordinates | Half-life ($T_{80}$, hr)[1] |
|---|---|---|---|---|---|---|---|
| Example 1 | BD1/MADN | Compound 1 | 700 | 13 | 4.9 | (0.15, 0.12) | 236 |
| Example 2 | BD1/MADN | Compound 9 | 700 | 13 | 4.8 | (0.15, 0.11) | 268 |
| Example 3 | BD1/MADN | Compound 11 | 700 | 11 | 4.5 | (0.15, 0.12) | 350 |
| Example 4 | BD1/MADN | Compound 20 | 700 | 11 | 4.6 | (0.15, 0.12) | 334 |
| Example 5 | BD1/MADN | Compound 21 | 700 | 12 | 4.4 | (0.15, 0.12) | 302 |
| Comparative Example 1 | BD1/MADN | Alq$_3$ | 700 | 16 | 5.4 | (0.15, 0.12) | 52 |
| Comparative Example 2 | BD1/MADN | Compound C-1 | 700 | 15 | 5.2 | (0.15, 0.12) | 112 |
| Comparative Example 3 | BD1/MADN | NTAZ | 700 | 18 | 6.1 | (0.15, 0.12) | 48 |

$T_{80}$[1] indicates the time taken until an initial luminance (700 nit) of the device at a measurement current density reduced to about 80% of the initial luminance.

Referring to Table 1, the organic light-emitting devices of Examples 1 to 5 were found to have better performance in terms of driving voltage, luminance (as would be seen by comparing luminance at constant potential), efficiency (as inferred from lower current densities at constant luminance), and lifetime, as compared with the organic light-emitting devices of Comparative Examples 1 to 3.

As described above, according to the one or more of the above embodiments of the present invention, an organic light-emitting device including the condensed cyclic compound of Formula 1 above may have improved performance, for example, a low driving voltage, a high efficiency, and a long lifetime.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A condensed cyclic compound of Formula 1 below:

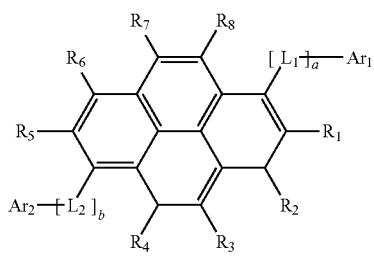

Formula 1 Ar$_1$ and Ar$_2$ in Formula 1 being each independently one of a hydrogen atom, a substituted or unsubstituted $C_6$-$C_{60}$ aryl group, a substituted or unsubstituted $C_2$-$C_{60}$ heteroaryl group, and a substituted or unsubstituted $C_1$-$C_{60}$ arylamino group, at least one of Ar$_1$ and Ar$_2$ being a substituent represented by Formula 2F below:

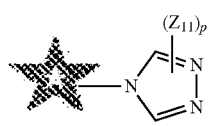

Formula 2F, $Z_{11}$ being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other;

p being an integer selected from 1 to 4;

★ indicating a binding site;

$L_1$ and $L_2$ in Formula 1 being each independently one of a substituted or unsubstituted $C_1$-$C_{60}$ alkylene group, a substituted or unsubstituted $C_3$-$C_{60}$ cycloalkylene group, a substituted or unsubstituted $C_2$-$C_{60}$ alkenylene group, a substituted or unsubstituted $C_5$-$C_{60}$ cycloalkenylene group, a substituted or unsubstituted $C_2$-$C_{60}$ alkynylene group, a substituted or unsubstituted $C_5$-$C_{60}$ cycloalkynylene group, a substituted or unsubstituted $C_6$-$C_{60}$ arylene group and a substituted or unsubstituted $C_5$-$C_{60}$ heteroarylene group;

a and b in Formula 1 being each independently 0 or 1; and $R_1$ to $R_8$ in Formula 1 being each independently one of a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, a substituted or unsubstituted $C_6$-$C_{60}$ arylthio group, —N($Q_1$)($Q_2$) and —Si($Q_3$)($Q_4$)($Q_5$) (where $Q_1$ to $Q_5$ are each independently one of a $C_1$-$C_{60}$ alkyl group, a $C_1$-$C_{60}$ alkoxy group, a $C_6$-$C_{60}$ aryl group, and a $C_2$-$C_{60}$ heteroaryl group).

2. The condensed cyclic compound of claim 1, $Ar_1$ and $Ar_2$ being each independently one of a hydrogen atom, a substituted or unsubstituted phenyl group, a substituted or unsubstituted biphenyl group, a substituted or unsubstituted terphenyl group, a substituted or unsubstituted pentaphenyl group, a substituted or unsubstituted naphthyl group, a substituted or unsubstituted anthryl group, a substituted or unsubstituted pentalenyl group, a substituted or unsubstituted indenyl group, a substituted or unsubstituted azulenyl group, a substituted or unsubstituted indacenyl group, a substituted or unsubstituted acenaphthyl group, a substituted or unsubstituted heptalenyl group, a substituted or unsubstituted phenalenyl group, a substituted or unsubstituted fluorenyl group, a substituted or unsubstituted phenanthrenyl group, a substituted or unsubstituted fluoranthenyl group, a substituted or unsubstituted pyrenyl group, a substituted or unsubstituted naphthacenyl group, a substituted or unsubstituted chrysenyl group, a substituted or unsubstituted triphenylenyl group, a substituted or unsubstituted perylenyl group, a substituted or unsubstituted picenyl group, a substituted or unsubstituted hexacenyl group, a substituted or unsubstituted spiro-fluorenyl group, a substituted or unsubstituted phenoxy group, a substituted or unsubstituted pyrrolyl group, a substituted or unsubstituted furyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted triazolyl group, a substituted or unsubstituted tetrazolyl group, a substituted or unsubstituted oxadiazolyl group, a substituted or unsubstituted a pyridyl group, a substituted or unsubstituted a pyrimidinyl group, a substituted or unsubstituted pyrazinyl group, a substituted or unsubstituted pyridazinyl group, a substituted or unsubstituted triazinyl group, a substituted or unsubstituted pyranyl group, a substituted or unsubstituted thiophenyl group, a substituted or unsubstituted thiazolyl group, a substituted or unsubstituted isothiazolyl group, a substituted or unsubstituted indolyl group, a substituted or unsubstituted isoindolyl group, a substituted or unsubstituted indolizinyl group, a substituted or unsubstituted benzofuryl group, a substituted or unsubstituted isobenzofuryl group, a substituted or unsubstituted indazolyl group, a substituted or unsubstituted benzimidazolyl group, a substituted or unsubstituted benzoxazolyl group, a substituted or unsubstituted benzisoxazolyl group, a substituted or unsubstituted imidazopyridyl group, a substituted or unsubstituted purinyl group, a substituted or unsubstituted quinolyl group, a substituted or unsubstituted isoquinolyl group, a substituted or unsubstituted phthalazinyl group, a substituted or unsubstituted quinazolinyl group, a substituted or unsubstituted quinoxalinyl group, a substituted or unsubstituted naphthyridinyl group, a substituted or unsubstituted cinnolinyl group, a substituted or unsubstituted benzothiophenyl group, a substituted or unsubstituted benzothiazolyl group, a substituted or unsubstituted carbazolyl group, a substituted or unsubstituted pyridoindolyl group, a substituted or unsubstituted dibenzofuryl group, a substituted or unsubstituted phenanthridinyl group, a substituted or unsubstituted benzoquinolyl group, a substituted or unsubstituted phenazinyl group, and a substituted or unsubstituted dibenzothiophenyl group.

3. The condensed cyclic compound of claim 1, $Ar_1$ and $Ar_2$ being each independently one of a hydrogen atom and a substituent represented by one of Formulae 2A to 2G below:

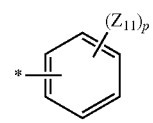

Formula 2A

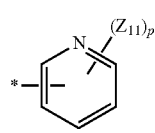

Formula 2B

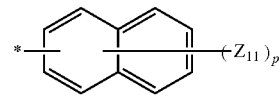

Formula 2C

-continued

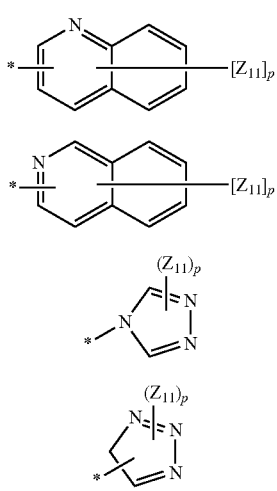

$Z_{11}$ being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other;

p being an integer selected from 1 to 7; and

* indicates a binding site.

4. The condensed cyclic compound of claim 1, $Ar_1$ and $Ar_2$ being each independently a group represented by one of Formulae 3A to 3J, at least one of $Ar_1$ and $Ar_2$ being a group represented by Formula 3J:

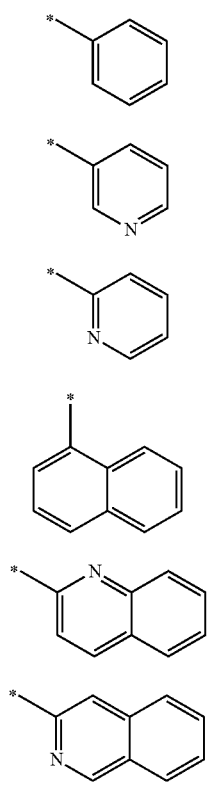

-continued

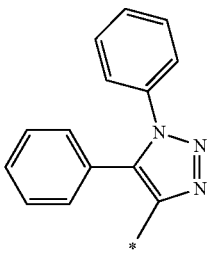

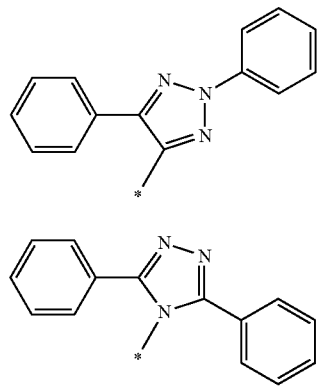

* in Formulae 3A to 3J indicating a binding site.

5. The condensed cyclic compound of claim 1, $L_1$ and $L_2$ being each independently one of a substituted or unsubstituted phenylene group, a substituted or unsubstituted biphenylene group, a substituted or unsubstituted terphenylene group, a substituted or unsubstituted pentaphenylene group, a substituted or unsubstituted a naphthyl group, a substituted or unsubstituted pentalenylene group, a substituted or unsubstituted indenylene group, a substituted or unsubstituted azulenylene group, a substituted or unsubstituted indacenyl group, a substituted or unsubstituted acenaphthyl group, a substituted or unsubstituted heptalenylene group, a substituted or unsubstituted phenalenylene group, a substituted or unsubstituted fluorenylene group, a substituted or unsubstituted phenanthrenylene group, a substituted or unsubstituted an anthryl group, a substituted or unsubstituted fluoranthenylene group, a substituted or unsubstituted pyrenylene group, a substituted or unsubstituted naphthacenylene group, a substituted or unsubstituted chrysenylene group, a substituted or unsubstituted triphenylenylene group, a substituted or unsubstituted perylenylene group, a substituted or unsubstituted picenylene group, a substituted or unsubstituted hexacenylene group, a substituted or unsubstituted spiro-fluorenylene group, a substituted or unsubstituted phenoxy group, a substituted or unsubstituted pyrrolyl group, a substituted or unsubstituted furyl group, a substituted or unsubstituted pyrazolyl group, a substituted or unsubstituted imidazolyl group, a substituted or unsubstituted oxazolyl group, a substituted or unsubstituted isoxazolyl group, a substituted or unsubstituted triazolyl group, a substituted or unsubstituted tetrazolyl group, a substituted or unsubstituted oxadiazolyl group, a substituted or unsubstituted a pyridyl group, a substituted or unsubstituted pyrimidinylene group, a substituted or unsubstituted pyrazinylene group, a substituted or unsubstituted pyridazinylene group, a substituted or unsubstituted triazinylene group, a substituted or unsubstituted pyranylene group, a substituted or unsubstituted thiophenylene group, a substituted or unsubstituted thiazolyl group, a substituted or unsubstituted isothiazolyl group, a substituted or unsubstituted indolyl group, a substituted or unsubstituted isoindolyl group, a substituted or unsubstituted indolizinylene group, a substituted or unsubstituted benzofuryl group, a substituted or unsubstituted isobenzofuryl group, a substituted or unsubstituted indazolyl group, a substituted or unsubstituted benzimidazolyl group, a substituted or unsubstituted benzoxazolyl group, a substituted or unsubstituted benzisoxazolyl group, a substituted or unsubstituted imidazopyridyl group, a substituted or unsubstituted purinylene group, a substituted or unsubstituted a quinolyl group, a substituted or unsubstituted isoquinolyl group, a substituted or unsubstituted phthalazinylene group, a substituted or unsubstituted quinazolinylene group, a substituted or unsubstituted quinoxalinylene group, a substituted or unsubstituted naphthyridinylene group, a substituted or unsubstituted cinnolinylene group, a substituted or unsubstituted benzothiophenylene group, a substituted or unsubstituted benzothiazolyl group, a substituted or unsubstituted a carbazolyl group, a substituted or unsubstituted pyridoindolyl group, a substituted or unsubstituted dibenzofuryl group, a substituted or unsubstituted phenanthridinylene group, a substituted or unsubstituted benzoquinolyl group, a substituted or unsubstituted phenazinylene group, and a substituted or unsubstituted dibenzothiophenylene group.

6. The condensed cyclic compound of claim 1, $L_1$ and $L_2$ being each independently one of a substituted or unsubstituted phenylene group, a substituted or unsubstituted naphthyl group, a substituted or unsubstituted pyridyl group, a substituted or unsubstituted pyrimidinylene group, a substituted or unsubstituted pyrazinylene group, and a substituted or unsubstituted pyridazinylene group.

7. The condensed cyclic compound of claim 1, $R_1$ to $R_8$ being each independently one of a hydrogen atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a naphthyl group, an anthryl group, a fluorenyl group, a dibenzofuranyl group, and a dibenzothiophenyl group; and
 a $C_1$-$C_{20}$ alkyl group, a $C_1$-$C_{20}$ alkoxy group, a phenyl group, a naphthyl group, an anthryl group, a fluorenyl group, a dibenzofuranyl group, and a dibenzothiophenyl group that are substituted with at least one of a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof.

8. The condensed cyclic compound of claim 1, $R_1$ to $R_8$ being each independently one of a hydrogen atom, a halogen atom, a methyl group, an ethyl group, a propyl group, a butyl group, a methoxy group, an ethoxy group, a propoxy group, a butoxy group, and a pentoxy group.

9. The condensed cyclic compound of claim 1, $Ar_1$ and $Ar_2$ being each independently one of a hydrogen atom and a substituent represented by one of Formulae 2A to 2G below:

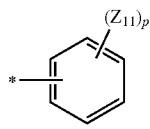

Formula 2A

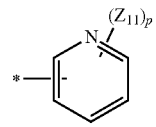

Formula 2B

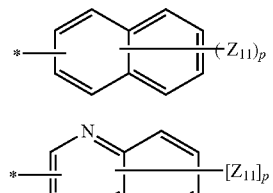

Formula 2C

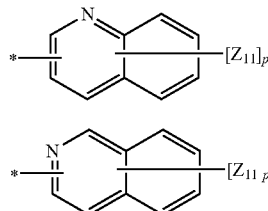

Formula 2D

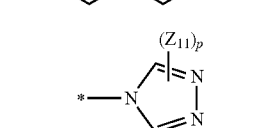

Formula 2E

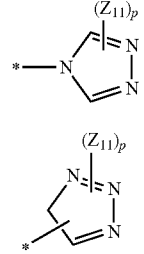

Formula 2F

Formula 2G

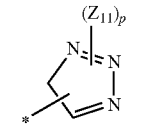

$Z_{11}$ in Formulae 2A to 2G being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group, a plurality of $Z_{11}$s being identical to or different from each other; p being an integer from 1 to 7; and * indicating a binding site;

$L_1$ and $L_2$ being each independently one of a phenylene group and a naphthyl group; and a phenylene group and a naphthyl group that are substituted with one of a halogen atom, a hydroxy group, a cyano group, a methyl group, an ethyl group, a propyl group, a butyl group, a methoxy group and an ethoxy group; and $R_1$ to $R_8$ being one of a hydrogen atom, a halogen atom, a hydroxy group, a cyano group, a methyl group, an ethyl group, a propyl group, a butyl group, a methoxy group, an ethoxy group, a phenyl group, a naphthyl group, an anthryl group, a pyridyl group, a fluorenyl group, and a quinolyl group.

10. The condensed cyclic compound of claim 1, $Ar_1$ and $Ar_2$ being each independently a group represented by one of Formulae 3A to 3J, at least one of $Ar_1$ and $Ar_2$ being a group represented by Formula 3J:

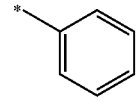

Formula 3A

-continued
Formula 3B
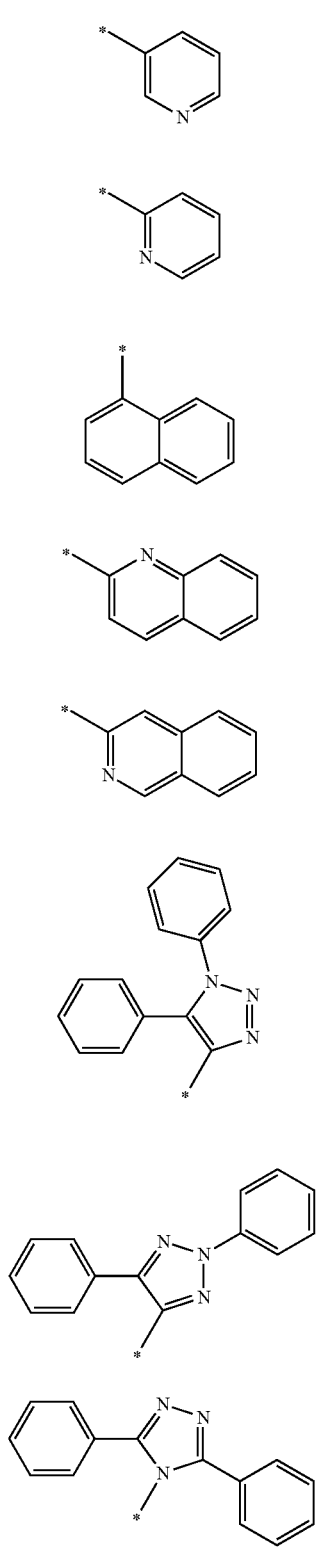
Formula 3C
Formula 3E
Formula 3F
Formula 3G
Formula 3H
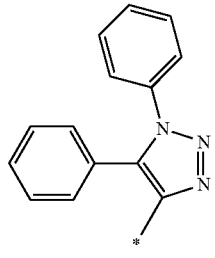
Formula 3I
Formula 3J
L₁ and L₂ being each independently one of a phenylene group and a naphthylene group; and $R_1$ to $R_8$ being hydrogen atoms.
11. The condensed cyclic compound of claim 1, the condensed cyclic compound being one of Compounds 1, 4 and 8 to 21 below:
1
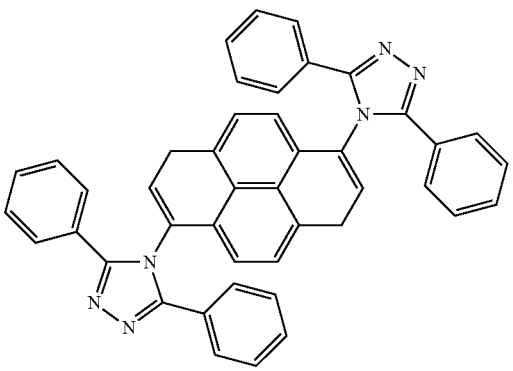
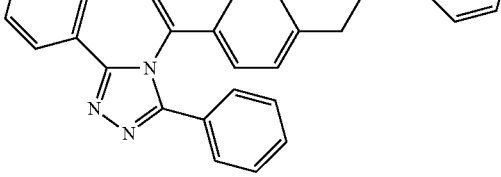
8
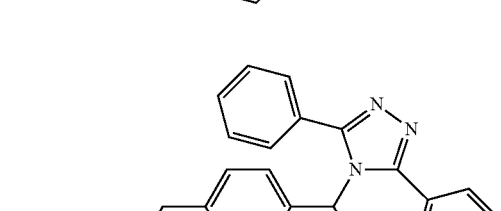
9
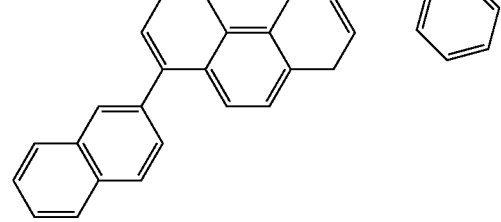
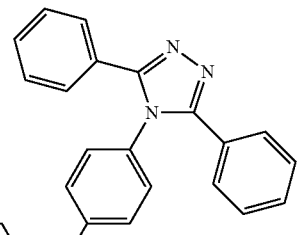
10
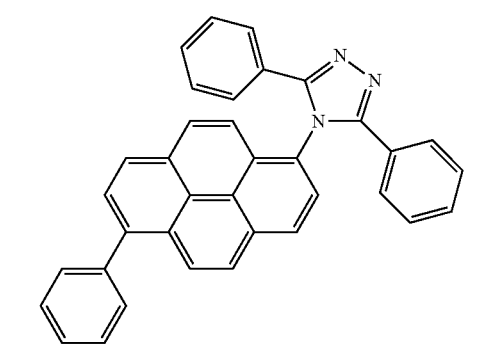

11
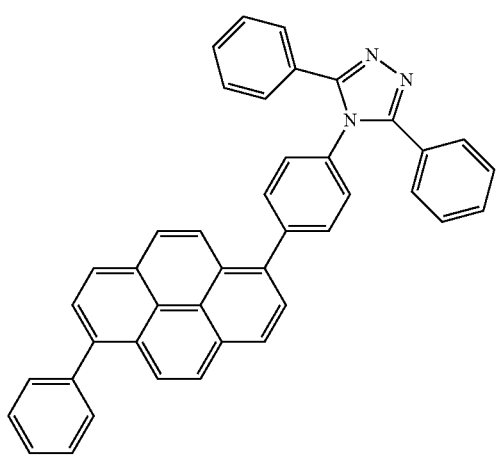
12
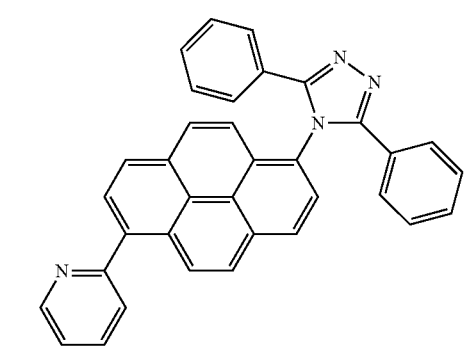
13
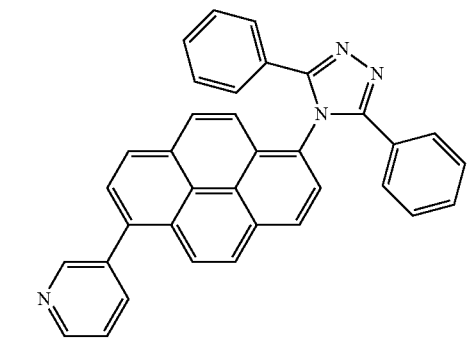
14
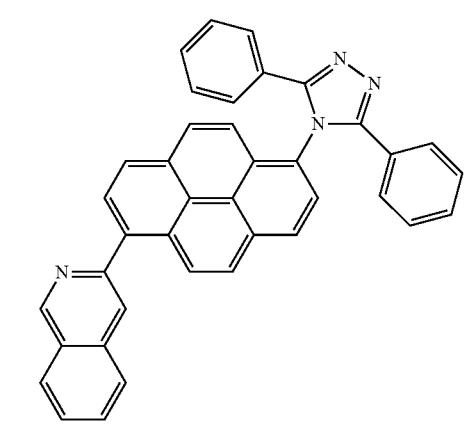
15
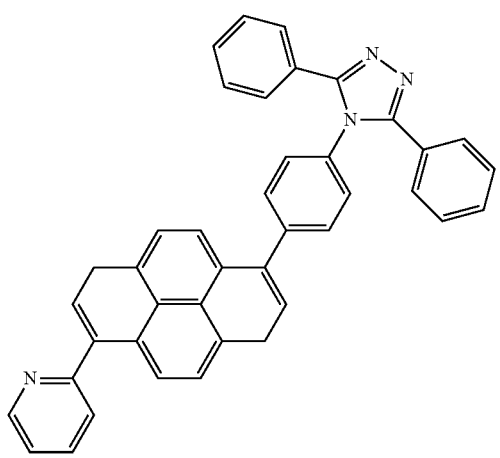
16
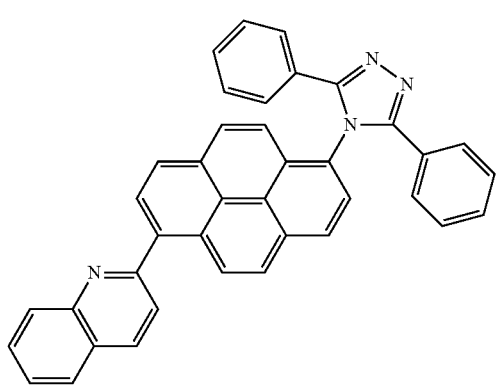
17
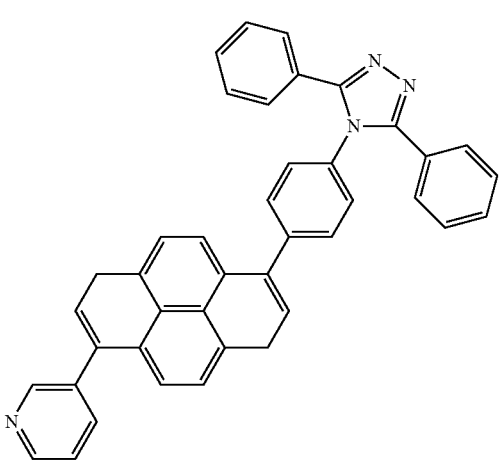

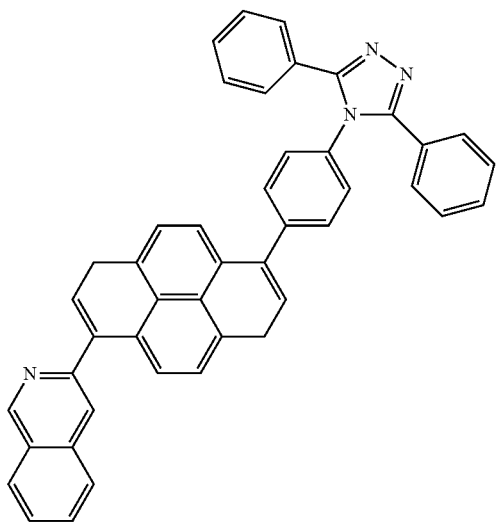

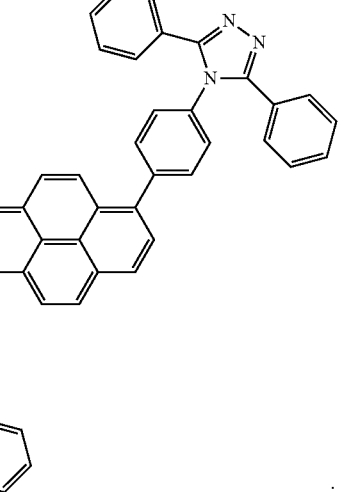

12. An organic light-emitting device comprising:
a substrate;
a first electrode disposed on the substrate;
a second electrode disposed opposite to the first electrode; and
an organic layer disposed between the first electrode and the second electrode,
the organic layer comprising at least one of the condensed cyclic compounds of claim 1.

13. The organic light-emitting device of claim 12, the organic layer comprising at least one of a hole injection layer, a hole transport layer, a hole injection and transport layer having both hole injection and hole transport capabilities, an emission layer, an electron injection layer, an electron transport layer, and an electron injection and transport layer having both electron injection and electron transport capabilities.

14. The organic light-emitting device of claim 13, the organic layer comprising at least one of the emission layer, the electron injection layer, the electron transport layer, and the electron injection and transport layer, at least one of the emission layer, the electron injection layer, the electron transport layer, and the electron injection and transport layer comprising the condensed cyclic compound.

15. The organic light-emitting device of claim 14, the organic layer comprising the emission layer, the emission layer comprising the condensed cyclic compound.

16. The organic light-emitting device of claim 15, the organic layer comprising the emission layer, the emission layer comprising an organometallic compound including at least one of iridium (Ir), platinum (Pt), osmium (Os), rhenium (Re), titanium (Ti), zirconium (Zr), hafnium (Hf), europium (Eu), terbium (Tb) and thulium (Tm).

17. The organic light-emitting device of claim 13, at least one of the hole injection layer, the hole transport layer and the hole injection and transport layer disposed between the first electrode and the organic layer, at least one of the hole injection layer, the hole transport layer and the hole injection and transport layer further comprising a charge-generating material.

18. The organic light-emitting device of claim 17, the charge-generating material being a p-type dopant.

* * * * *